(12) United States Patent
Manwill et al.

(10) Patent No.: US 12,059,352 B2
(45) Date of Patent: Aug. 13, 2024

(54) EXPANDING, CONFORMING INTERBODY SPACER

(71) Applicant: Nexus Spine, L.L.C., Salt Lake City, UT (US)

(72) Inventors: Daniel Manwill, Riverton, UT (US); Peter Halverson, Draper, UT (US)

(73) Assignee: Nexus Spine, LLC, Salt Lake City, UT (US)

( * ) Notice: Subject to any disclaimer, the term of this patent is extended or adjusted under 35 U.S.C. 154(b) by 38 days.

(21) Appl. No.: 18/089,441

(22) Filed: Dec. 27, 2022

(65) Prior Publication Data

US 2023/0134455 A1 May 4, 2023

Related U.S. Application Data

(62) Division of application No. 16/584,921, filed on Sep. 26, 2019, now Pat. No. 11,534,305.

(60) Provisional application No. 62/751,432, filed on Oct. 26, 2018, provisional application No. 62/736,924, filed on Sep. 26, 2018.

(51) Int. Cl.
*A61F 2/44* (2006.01)
*A61F 2/30* (2006.01)

(52) U.S. Cl.
CPC .......... *A61F 2/30771* (2013.01); *A61F 2/442* (2013.01); *A61F 2/447* (2013.01); *A61F 2002/30476* (2013.01); *A61F 2002/30556* (2013.01); *A61F 2002/30579* (2013.01); *A61F 2002/30581* (2013.01); *A61F 2002/30891* (2013.01)

(58) Field of Classification Search
CPC ................................................. A61F 2/44–447
See application file for complete search history.

(56) References Cited

U.S. PATENT DOCUMENTS

| | | | | |
|---|---|---|---|---|
| 5,123,926 | A * | 6/1992 | Pisharodi | A61F 2/442 606/279 |
| 9,414,934 | B2 * | 8/2016 | Cain | A61F 2/4425 |
| 9,532,883 | B2 * | 1/2017 | McLuen | A61F 2/28 |
| 9,937,050 | B2 * | 4/2018 | Dinville | A61F 2/4455 |
| 10,219,914 | B2 * | 3/2019 | Faulhaber | A61F 2/447 |
| 2005/0049590 | A1 * | 3/2005 | Alleyne | A61F 2/442 606/279 |
| 2006/0095136 | A1 * | 5/2006 | McLuen | A61F 2/4455 623/17.11 |
| 2012/0046748 | A1 * | 2/2012 | Weiman | A61F 2/4611 623/17.16 |
| 2012/0303124 | A1 * | 11/2012 | McLuen | A61F 2/4455 623/17.16 |

(Continued)

*Primary Examiner* — Eduardo C Robert
*Assistant Examiner* — Steven J Cotroneo
(74) *Attorney, Agent, or Firm* — Bryant J. Keller; Kirton McConkie

(57) ABSTRACT

An expanding, conforming interbody implant includes a plurality of superior and a plurality of inferior segments. The segments are adapted to individually expand, contact, and conform to endplates of vertebral bodies to distribute forces equally over the implant and across the vertebral endplates. Once a proper extension of the segments has been achieved, the segments are locked in position. The implant has a stiffness that approximates the stiffness of bone, and the implant minimizes problems with subsidence, endplate fractures, and stress shielding.

19 Claims, 31 Drawing Sheets

(56) References Cited

U.S. PATENT DOCUMENTS

2013/0197647 A1* 8/2013 Wolters .................. A61F 2/442
 623/17.16
2013/0304211 A1* 11/2013 Trautwein ............... A61L 27/04
 623/17.15

* cited by examiner

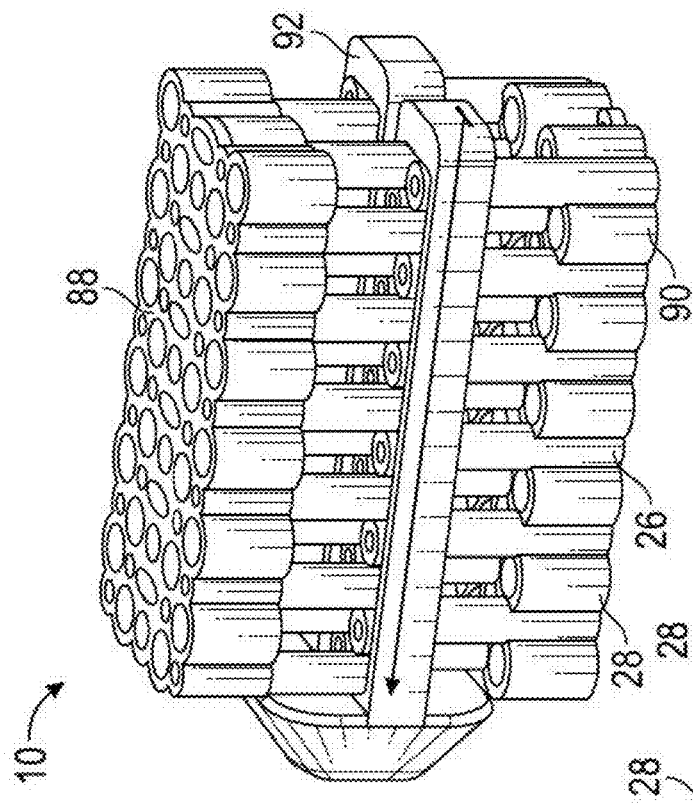
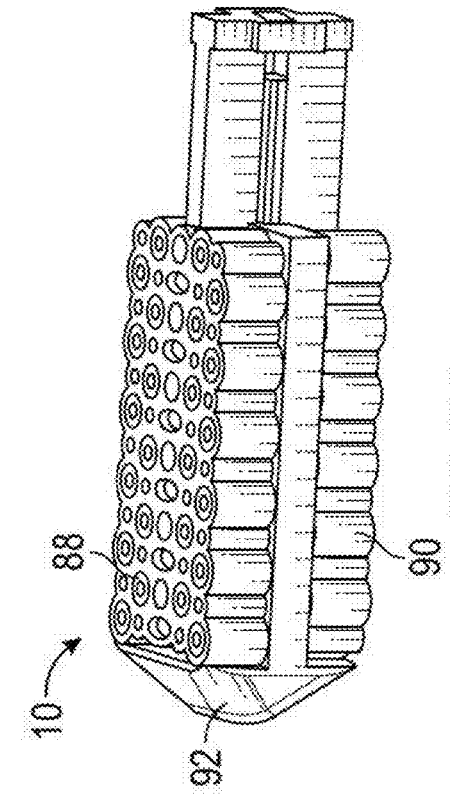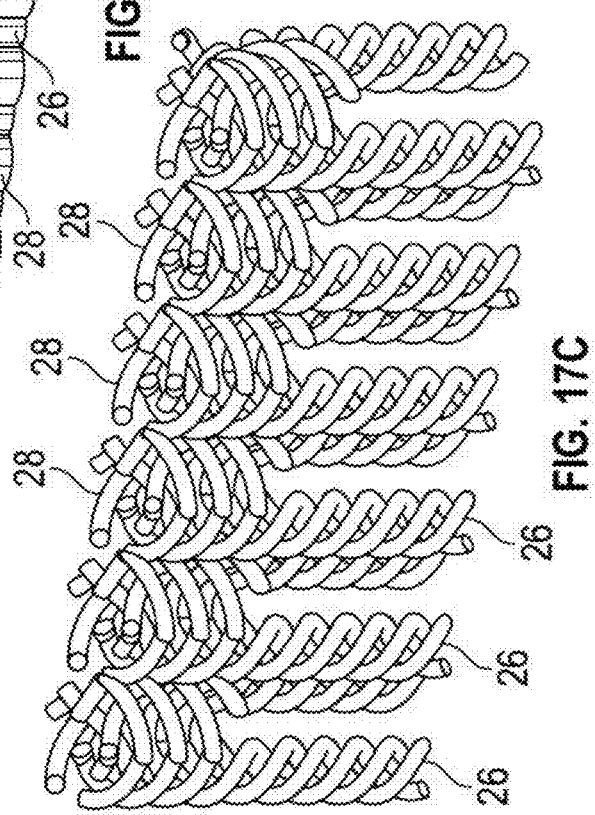

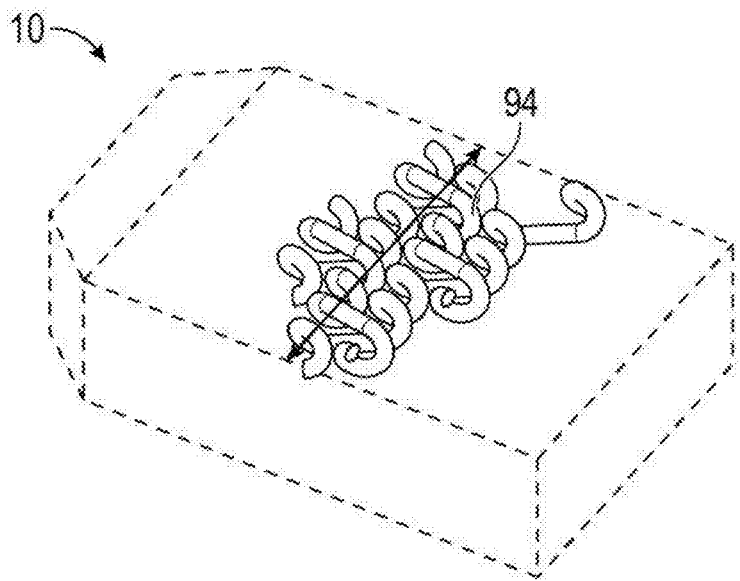
FIG. 18A
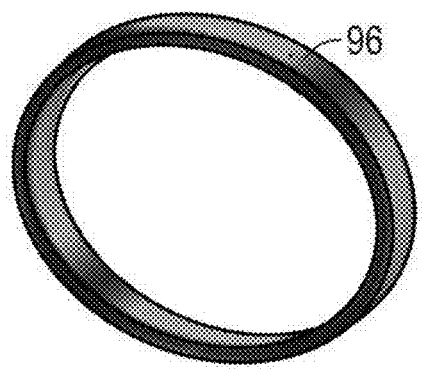
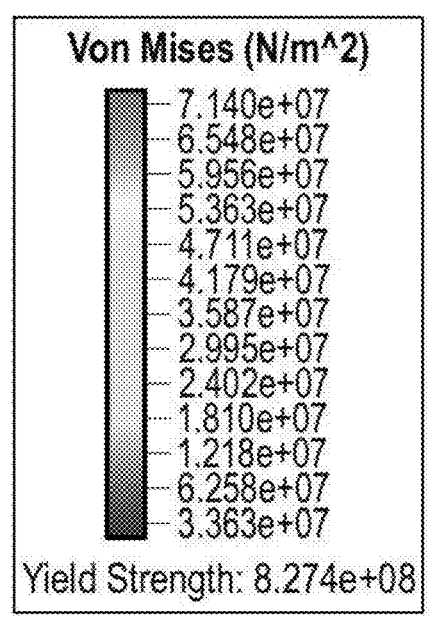
FIG. 18B
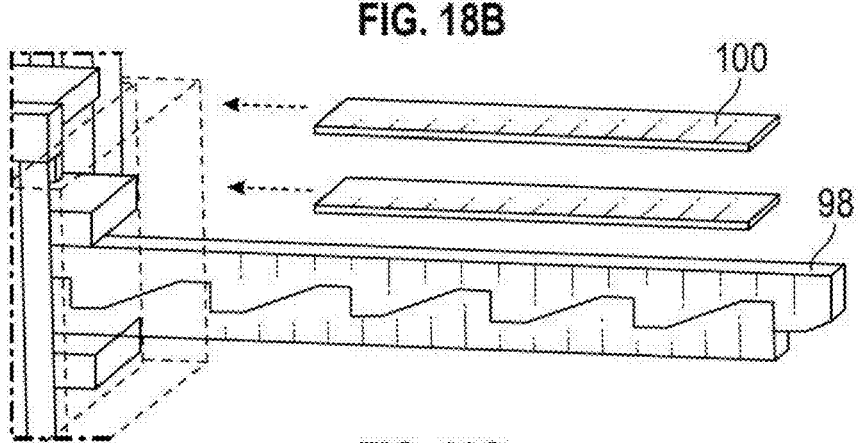
FIG. 18C

EXPANDING, CONFORMING INTERBODY SPACER

CROSS-REFERENCE TO RELATED APPLICATIONS

This application is a divisional of U.S. patent application Ser. No. 16/584,921, filed Sep. 26, 2019, and entitled "Expanding, Conforming Interbody Spacer", issued Dec. 27, 2022, as U.S. Pat. No. 11,534,305, which claims the benefit of U.S. Provisional Application No. 62/736,924, filed Sep. 26, 2018, and U.S. Provisional Application No. 62/751,432, filed Oct. 26, 2018.

BACKGROUND OF THE INVENTION

1. Field of the Invention

The present invention relates to surgical implants, and more particularly to interbody spacers for vertebral implants.

2. Background and Related Art

In the area of spinal implants, there are certain difficulties that remain unaddressed. In particular, the problems of subsidence, endplate fractures, and stress shielding remain problems that can cause intervertebral implants to fail or to have reduced effectiveness at achieving the desired implant goals. These problems are heightened by the difficulties in properly sizing implants: to ensure that a correctly sized implant is used, the doctor must be careful in selecting among available implants, and there are costs associated with carrying implants of multiple sizes to be available at the time of implant surgery. Accordingly, either the doctor or hospital must incur the cost of purchasing and holding in inventory a large number of implants of varying sizes to ensure that a correctly sized implant is available, or they must have a reduced number of implant sizes with the risk that an implant of the correct size will not be available, such that an incorrectly sized implant must be used with reduced effectiveness.

Additionally, depending on surgeon experience, it may be difficult for the surgeon to select among available implant sizes an implant of ideal size, and some trial-and-error efforts may be used to select among available implant sizes. Where this is done, however, either incorrectly sized, but tried, implants are contaminated and wasted, or are required to pass through a sterilization process before being reused, if even possible. Accordingly, such trial-and-error efforts result in increased costs to the surgeon and/or hospital, which must then be passed on to patients.

Even when surgeons are able to use correctly sized implants, such implants still rarely have proper physical characteristics to promote bone ingrowth and to minimize problems with subsidence, endplate fracture, and/or stress shielding. Current implants are rarely shaped to conform to the endplates where they are placed. Additionally, current implants typically have stiffnesses that are significantly different from the stiffness of the vertebral endplates where they are placed, such that any nonconformities between the endplates and the implant lead to locations of increased stress and implant failure.

Accordingly, for reasons such as these, existing interbody implants fail to satisfactorily meet the requirements desired by surgeons and patients.

BRIEF SUMMARY OF THE INVENTION

Implementations of the invention provide expandable, conformable interbody spacers, methods for manufacturing interbody spacers, and methods for using interbody spacers. In accordance with certain implementations of the invention, an expandable, conformable interbody implant includes a frame, a first plurality of endplate-contacting segments adapted to extend in a superior direction from the frame, a second plurality of endplate-contacting segments adapted to extend in an inferior direction from the frame and a locking mechanism adapted to lock the first plurality of endplate-contacting segments and the second plurality of endplate-contacting segments in a variety of extended positions.

In some implementations, the first plurality of endplate-contacting segments is adapted to contact and collectively conform to an inferior endplate of a first vertebral body and wherein the second plurality of endplate-contacting segments is adapted to contact and collectively conform to a superior endplate of a second vertebral body. In some implementations, a load between the inferior endplate and the anterior endplate is substantially equally distributed among the first and second pluralities of endplate-contacting segments.

In some implementations, the locking mechanism exerts a lateral compression force among the first and second pluralities of endplate-contacting segments. In some implementations, the locking mechanism exerts a lateral compression force between the first plurality of endplate-contacting segments, the second plurality of endplate-contacting segments, and a plurality of cross webs.

In some implementations, the first and second pluralities of endplate-contacting segments have a limited amount of lateral motion within the frame before the locking mechanism is engaged to lock the first and second pluralities of endplate-contacting segments in their extended positions. In some implementations, when the first and second pluralities of endplate-contacting segments are in a retracted position, the implant has a smaller vertical profile for insertion.

In some implementations, the first and second pluralities of endplate-contacting segments are each interlocked with adjacent segments while permitting relative superior-inferior motion therebetween. In some implementations, the first and second pluralities of endplate-contacting segments each include a plurality of segments extending along a length of the implant. In some implementations, the first and second pluralities of endplate-contacting segments each include a plurality of segments extending across a width of the implant.

In some implementations, the first and second pluralities of endplate-contacting segments have a stiffness approximating the stiffness of vertebral bone. In some implementations, the first and second pluralities of endplate-contacting segments have a coil pack construction.

In some implementations, the implant is formed of biocompatible substances.

In some implementations, the implant includes an expansion mechanism adapted to apply a superior-directed force to each of the first plurality of endplate-contacting segments and an inferior-directed force to each of the second plurality of endplate-contacting segments before the locking mechanism is engaged. In some implementations, the expansion mechanism is adapted to continue providing the superior-directed force and the inferior-directed force while the locking mechanism is engaged. In some implementations, the expansion mechanism includes a bladder disposed in an internal cavity of the implant. In some implementations, the expansion mechanism is a mechanism such as a bladder, a plurality of corrugated layers adapted to be moved between nested and offset positions, a plurality of springs, a wire disposed on a plurality of pulleys, a plurality of threaded cylinders, or a plurality of dimpled layers adapted to be moved between nested and offset positions.

In some implementations, the frame includes openings on opposite ends thereof to permit access to an internal space of the implant. In some implementations, the implant is adapted to permit application of increased forces in any of an anterior area, a posterior area, a right lateral area, or a left lateral area.

According to further implementations of the invention, a method for using an expanding, conforming interbody implant, includes a step of affixing an expanding, conforming interbody implant to an inserter, the implant including a frame, a first plurality of endplate-contacting segments adapted to extend in a superior direction from the frame, a second plurality of endplate-contacting segments adapted to extend in an inferior direction from the frame, and a locking mechanism adapted to lock the first plurality of endplate-contacting segments and the second plurality of endplate-contacting segments in a variety of extended positions. The method also includes steps of placing the implant in a desired location using the inserter while the first and second pluralities of endplate-contacting segments are in a retracted position, supplying a force that causes the first and second pluralities of endplate-contacting segments to extend and generally conform to surfaces above and below the implant, and engaging the locking mechanism to secure the first and second pluralities of endplate-contacting segments in extended and conforming positions.

BRIEF DESCRIPTION OF THE SEVERAL VIEWS OF THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

FIGS. 17A-17C illustrate aspects of an implant;

FIGS. 18A-18C illustrate features of certain implants;

DETAILED DESCRIPTION OF THE INVENTION

Figure 1A:
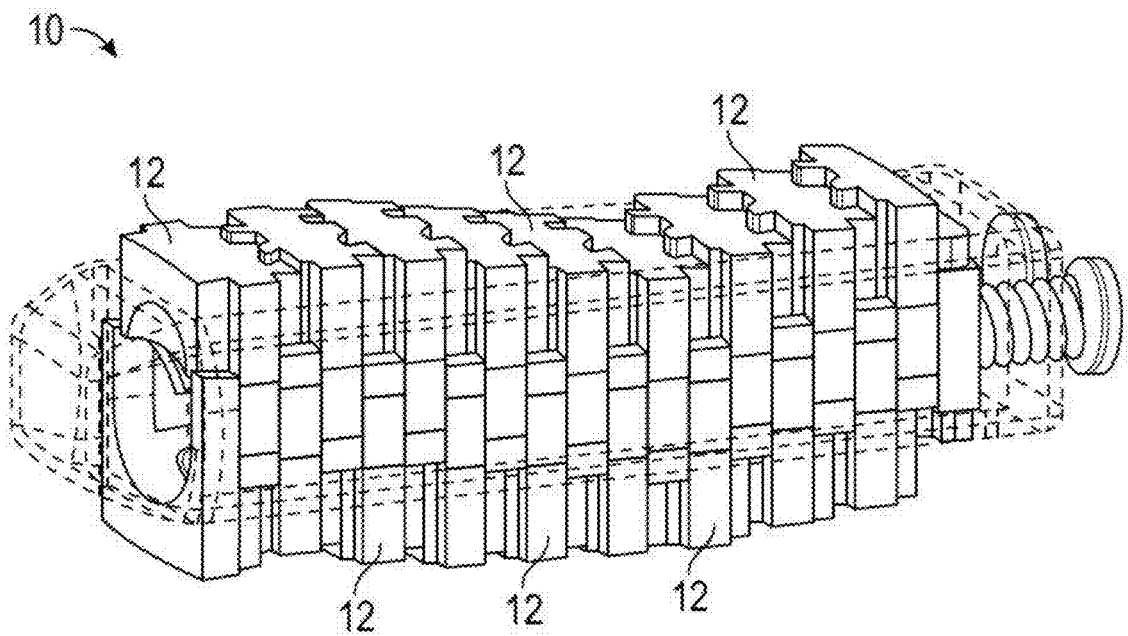
FIGS. 1A and 1B show perspective views of an illustrative implant.

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

What is needed is an interbody implant with the ability to conform to the endplate shape, thereby minimizing problems of subsidence, endplate fracture, and stress shielding. Such an implant may utilize expanding segmented portions to permit the surfaces of the implant to generally conform to the vertebral endplates above and below the interbody space. Additionally, an interbody implant with an ability to expand reduces the carrying or inventory cost of the hospital and/or surgeon while also reducing the need for trialing by the surgeon. When such implants also include correct stiffness, they further reduce the possibility of subsidence, endplate fracture, or stress shielding.

Embodiments of the invention provide expandable, conformable interbody spacers, methods for manufacturing interbody spacers, and methods for using interbody spacers. In accordance with certain embodiments of the invention, an expandable, conformable interbody implant includes a frame, a first plurality of endplate-contacting segments adapted to extend in a superior direction from the frame, a second plurality of endplate-contacting segments adapted to extend in an inferior direction from the frame and a locking mechanism adapted to lock the first plurality of endplate-contacting segments and the second plurality of endplate-contacting segments in a variety of extended positions.

In some embodiments, the first plurality of endplate-contacting segments is adapted to contact and collectively conform to an inferior endplate of a first vertebral body and wherein the second plurality of endplate-contacting segments is adapted to contact and collectively conform to a superior endplate of a second vertebral body. In some embodiments, a load between the inferior endplate and the anterior endplate is substantially equally distributed among the first and second pluralities of endplate-contacting segments.

In some embodiments, the locking mechanism exerts a lateral compression force among the first and second pluralities of endplate-contacting segments. In some embodiments, the locking mechanism exerts a lateral compression force between the first plurality of endplate-contacting segments, the second plurality of endplate-contacting segments, and a plurality of cross webs.

In some embodiments, the first and second pluralities of endplate-contacting segments have a limited amount of lateral motion within the frame before the locking mechanism is engaged to lock the first and second pluralities of endplate-contacting segments in their extended positions. In some embodiments, when the first and second pluralities of endplate-contacting segments are in a retracted position, the implant has a smaller vertical profile for insertion.

In some embodiments, the first and second pluralities of endplate-contacting segments are each interlocked with adjacent segments while permitting relative superior-inferior motion therebetween. In some embodiments, the first and second pluralities of endplate-contacting segments each include a plurality of segments extending along a length of the implant. In some embodiments, the first and second pluralities of endplate-contacting segments each include a plurality of segments extending across a width of the implant.

In some embodiments, the first and second pluralities of endplate-contacting segments have a stiffness approximating the stiffness of vertebral bone. In some embodiments, the first and second pluralities of endplate-contacting segments have a coil pack construction.

In some embodiments, the implant is formed of biocompatible substances.

In some embodiments, the implant includes an expansion mechanism adapted to apply a superior-directed force to each of the first plurality of endplate-contacting segments and an inferior-directed force to each of the second plurality of endplate-contacting segments before the locking mechanism is engaged. In some embodiments, the expansion mechanism is adapted to continue providing the superior-directed force and the inferior-directed force while the locking mechanism is engaged. In some embodiments, the expansion mechanism includes a bladder disposed in an internal cavity of the implant. In some embodiments, the expansion mechanism is a mechanism such as a bladder, a plurality of corrugated layers adapted to be moved between nested and offset positions, a plurality of springs, a wire disposed on a plurality of pulleys, a plurality of threaded cylinders, or a plurality of dimpled layers adapted to be moved between nested and offset positions.

In some embodiments, the frame includes openings on opposite ends thereof to permit access to an internal space of the implant. In some embodiments, the implant is adapted to permit application of increased forces in any of an anterior area, a posterior area, a right lateral area, or a left lateral area.

According to further embodiments of the invention, a method for using an expanding, conforming interbody implant, includes a step of affixing an expanding, conforming interbody implant to an inserter, the implant including a frame, a first plurality of endplate-contacting segments adapted to extend in a superior direction from the frame, a second plurality of endplate-contacting segments adapted to extend in an inferior direction from the frame, and a locking mechanism adapted to lock the first plurality of endplate-contacting segments and the second plurality of endplate-contacting segments in a variety of extended positions. The method also includes steps of placing the implant in a desired location using the inserter while the first and second pluralities of endplate-contacting segments are in a retracted position, supplying a force that causes the first and second pluralities of endplate-contacting segments to extend and generally conform to surfaces above and below the implant, and engaging the locking mechanism to secure the first and second pluralities of endplate-contacting segments in extended and conforming positions.

Figure 1B:
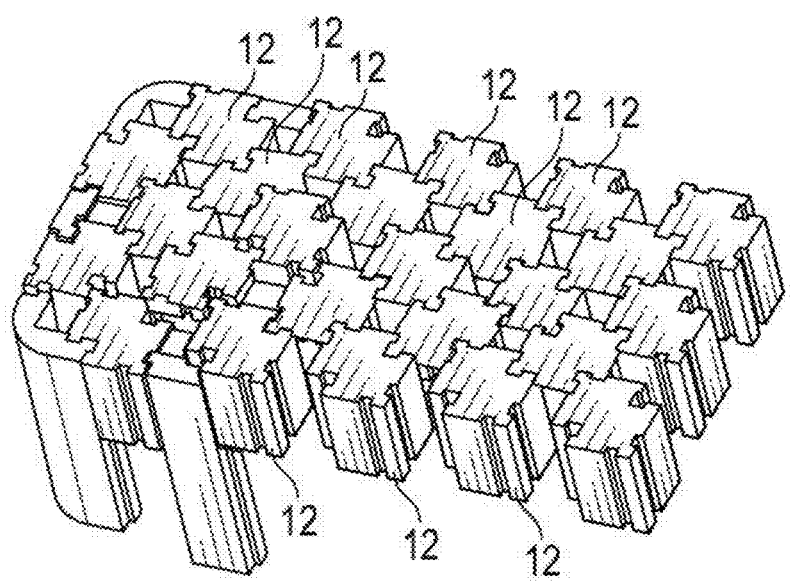

Existing interbody implant designs have at most one or two moving elements, allowing at best for two points of adjustment (e.g., height and lordosis). The innovative designs of embodiments of the implant 10 discussed herein use multiple height-independent segments 12 to conform to individuals' endplate shape, as is illustrated in FIGS. 1A and 1B. FIG. 1A illustrates one embodiment of the implant 10 having a plurality of height-independent segments 12 divided along the length of the implant. The illustrated embodiment shows how segments 12 are placed on both upper and lower surfaces of the implant 10 to allow conformity to both superior and inferior endplates of the intervertebral space.

FIG. 1B illustrates a portion of another embodiment of the implant 10 having a plurality of height-independent segments 12 divided along both the length and width of the implant. While not shown in this embodiment in FIG. 1B, the full implant 10 would have such segments 12 on both the upper and lower surfaces of the implant 10 to permit implant conformity to both the superior and inferior endplates of the intervertebral space.

Even where prior adjustable-height implants provided some adjustability for height or lordosis, the mechanisms for such adjustability had significant downsides. In particular, it was typical for such implants to use the same mechanical feature for lifting the implant or adjusting the height as for holding and carrying the patient load. This mechanical feature might be a ramp, wedge, or the like, but tended to collect the load to a very small portion of the implant, requiring it to be extremely strong and stiff, leading to subsidence and stress shielding.

Figure 2:
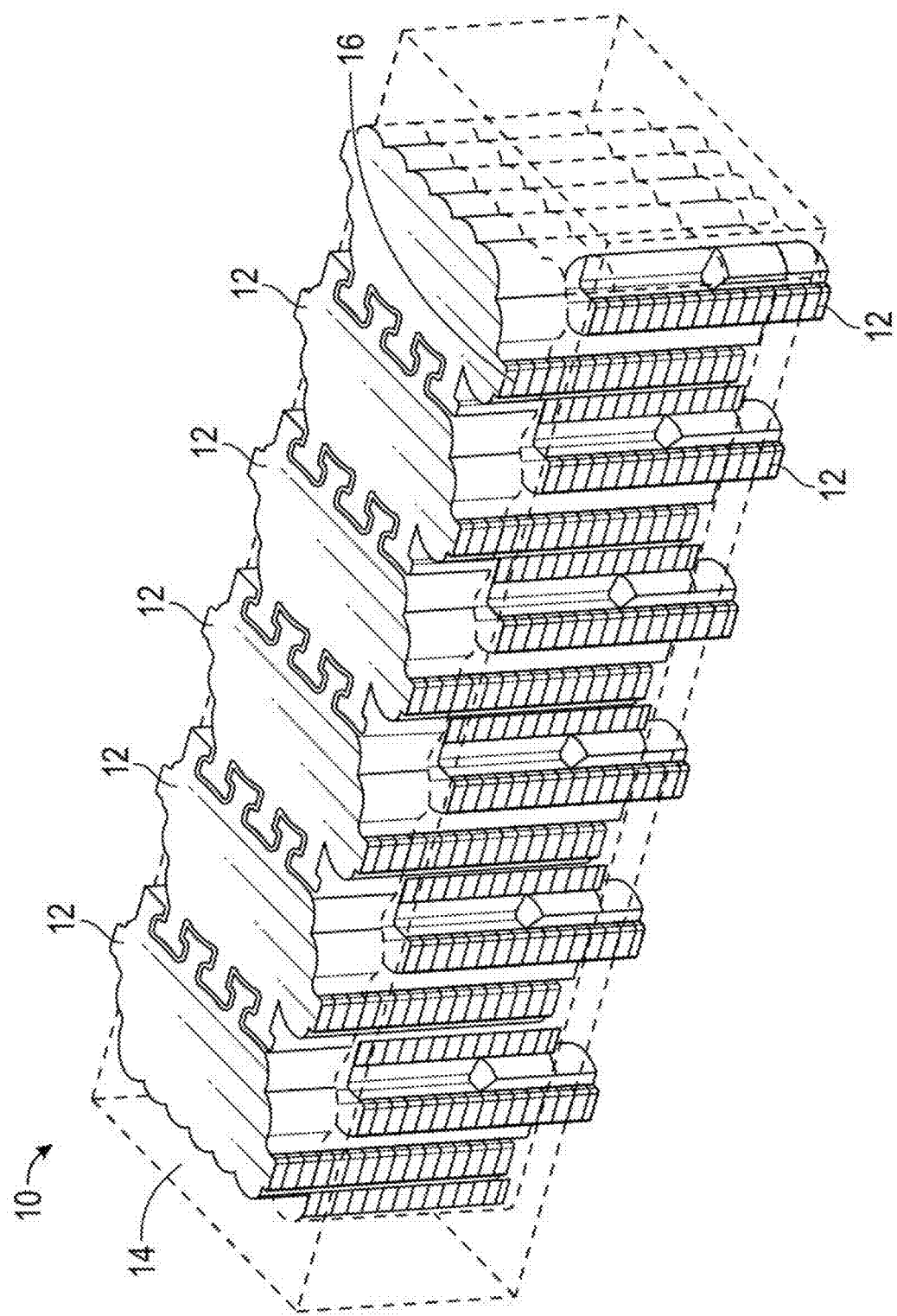
FIG. 2 shows a perspective transparent view of an illustrative implant.

Embodiments of the invention separate the conforming mechanism (the lift mechanism) from the shape-locking or height-locking mechanism. This separation allows the implant to have a reduced stiffness in the biological load path, thereby allowing the implant 10 to more-closely approximate the stiffness of bone. As illustrated in the embodiment shown in FIG. 2, in some embodiments, the segments 12 are lifted or separated into conformance with the vertebrae by a lift mechanism such as an inflatable bladder (not shown). Once the segments 12 are at the desired location (e.g., achieving a desired height and/or lordosis), a frame 14 of the implant 10 surrounding the segments is translated relative to the segments 12, such that teeth 16 of the lateral edges of the segments 12 engage corresponding teeth on portions of the inside surface of the frame 14, thereby providing multiple less-rigid load paths between the opposing segments 12 (e.g., in the superior-inferior axis). If desired in some embodiments, the lift mechanism may then be removed from the implant 10.

Figure 3:
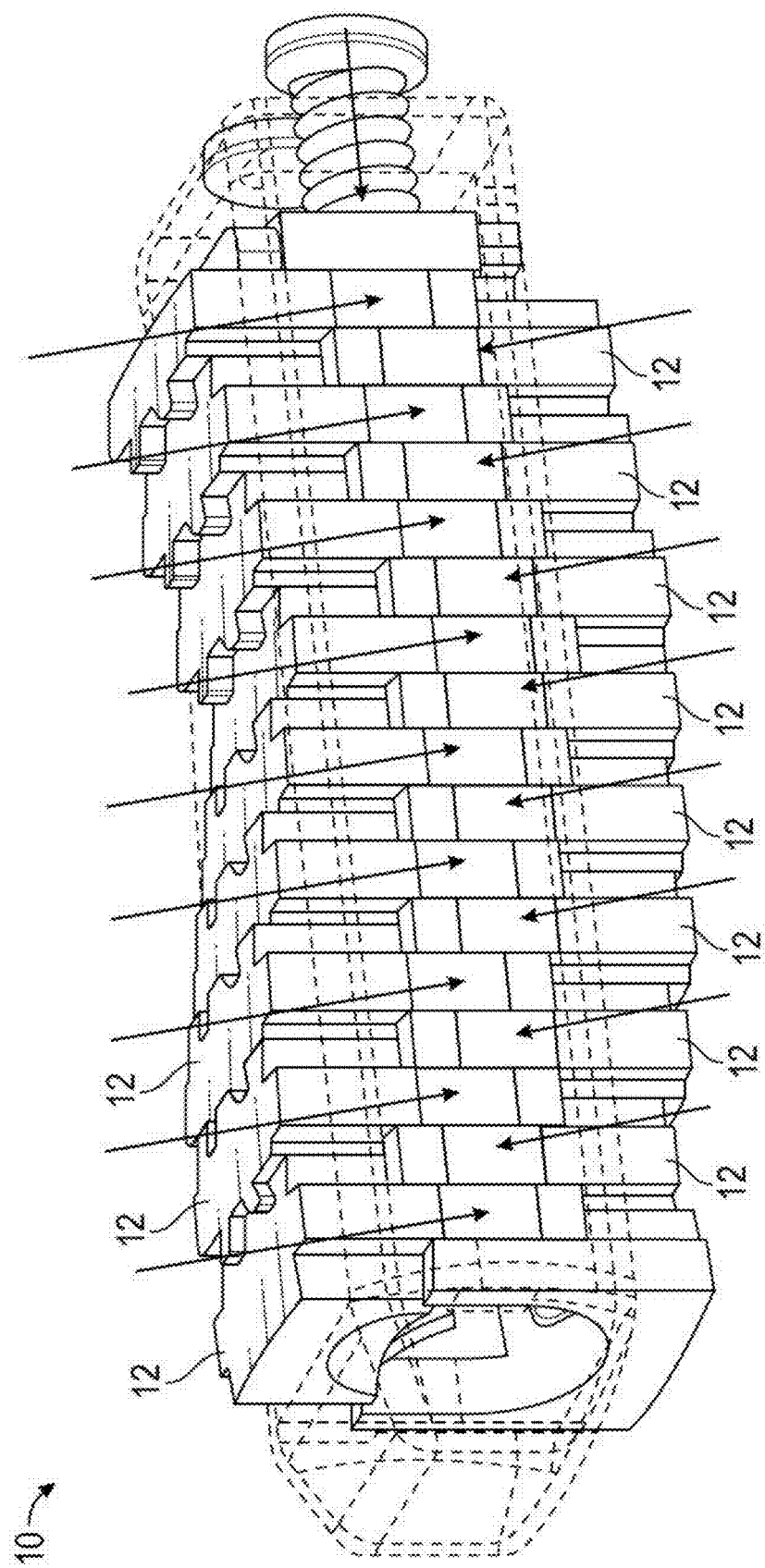
FIG. 3 shows a perspective partially-transparent view of an illustrative implant.
Figure 4:
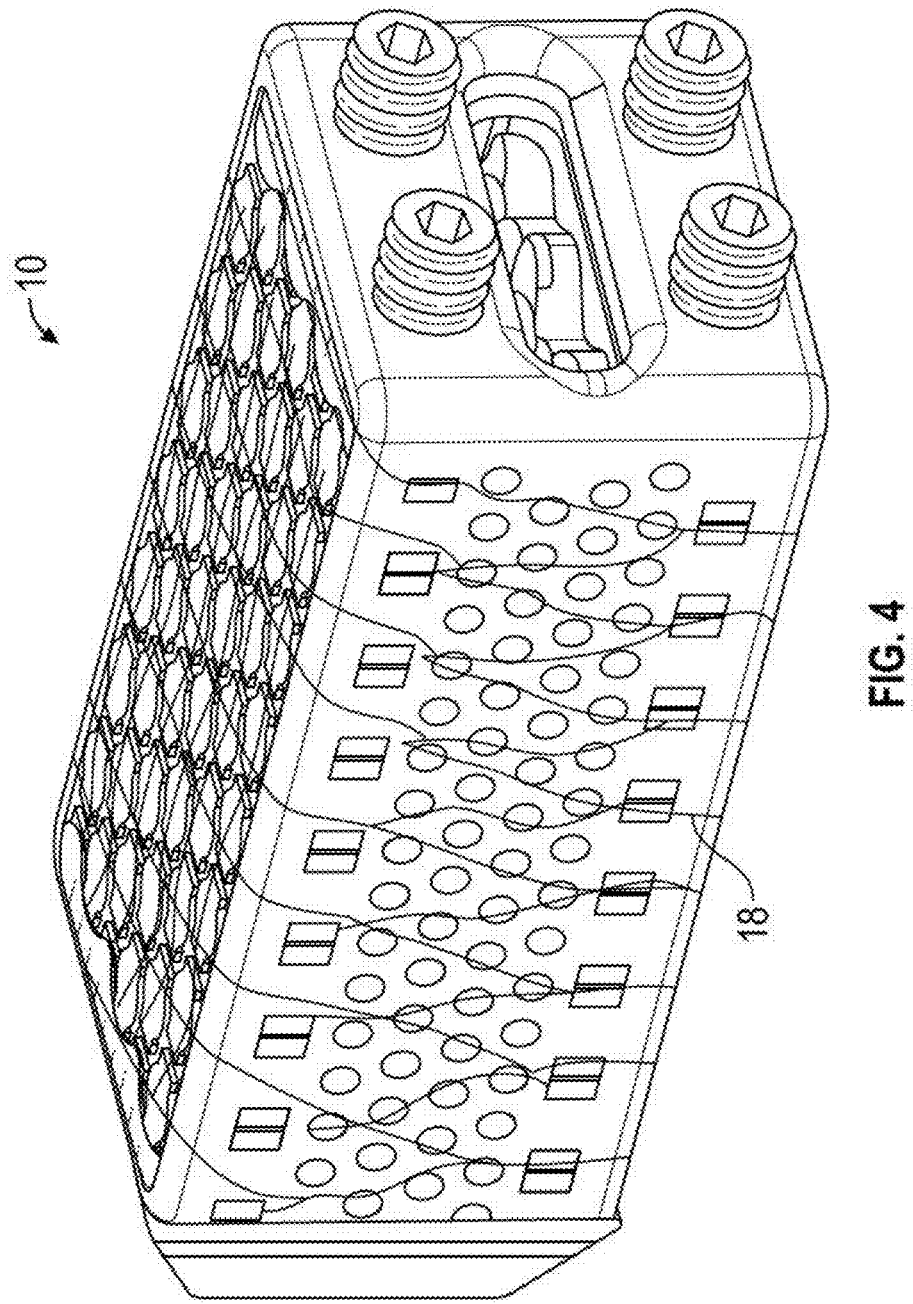
FIG. 4 shows a perspective view of an illustrative implant.
Figure 5:
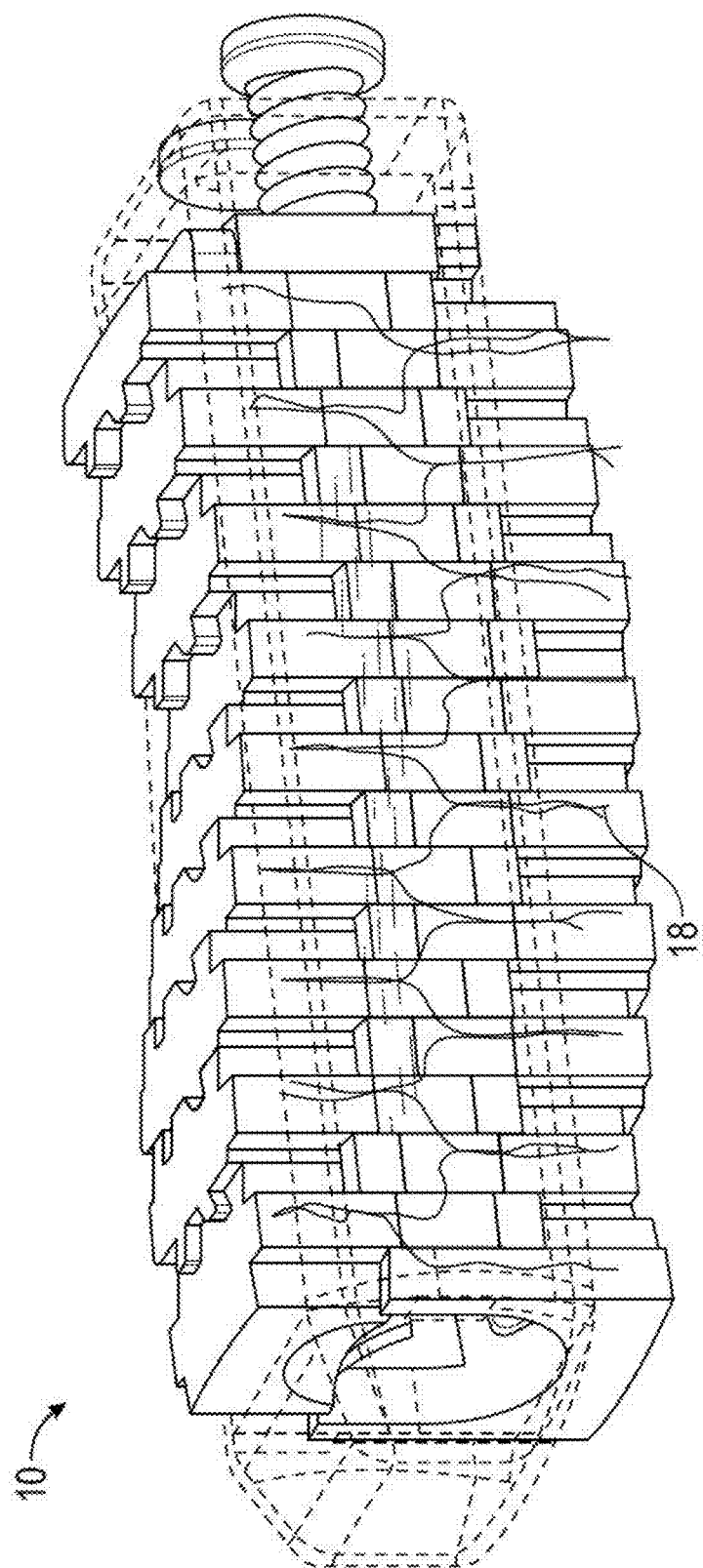
FIG. 5 shows a perspective partially-transparent view of an illustrative implant.

As another example, as illustrated in FIG. 3, in alternate embodiments, each segment 12 has a strut (indicated by the arrows) along each side thereof. The struts of adjacent segments 12 interdigitate with struts of segments 12 on the other side of the implant 10 (superior struts adjacent to inferior struts). A light clamping force through the stack of struts (e.g., in the lateral axis), the conformed shape is locked and superior-inferior loads are transmitted locally from endplate to endplate, rather than being collected into a single overly rigid structure.

By providing a design where forces are transmitted through the implant 10 in as many paths as possible, rather than by collecting forces into a single rigid frame structure, stress shielding is reduced. This is illustrated in FIGS. 5 and 6A-6E, which illustrate how embodiments of the implant 10 permit the distribution of load along a variety of load paths 18 from the conforming superior surface of the implant 10 to the conforming inferior surface of the implant 10.

Embodiments of the invention embrace the use of additive manufacturing techniques (e.g., 3D printing) that allow achievement of various design objectives, including the manufacture of interlocking segments 12 that remain interlocked but permit some measure of sliding relative to each other such that the individual segments 12 can conform to the vertebral endplates. In some embodiments, other than additive manufacturing techniques are used to manufacture some or all of the implant 10, including the segments 12 and/or the frame 14. In other embodiments, additive manufacturing techniques are used to manufacture both the segments 12 and the frame 14. Accordingly, embodiments of the invention are not limited to a single manufacturing technique.

FIGS. 6A-6E illustrate various illustrative embodiments of manners in which adjacent segments 12 may be made interlocking while allowing a certain amount of sliding motion relative to each other in a generally superior-inferior direction. Other manners of providing slidable interlocking have been illustrated in FIGS. 1-5, and the manners illustrated in the Figures are not intended to be exhaustive, but illustrative of manners in which slidable interlocking of adjacent segments may be achieved.

Figure 6A:
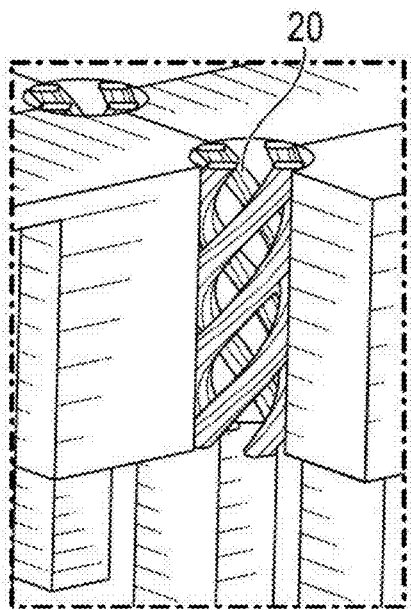
FIG. 6A-6E show perspective views of various mechanisms to interlock segments of an implant.
Figure 6B:
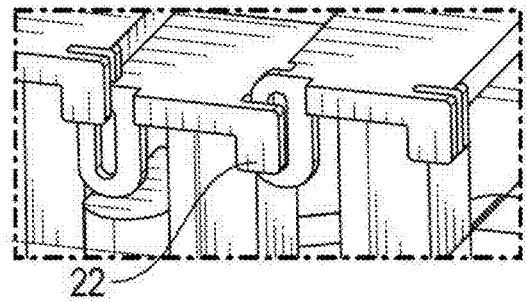
Figure 6C:
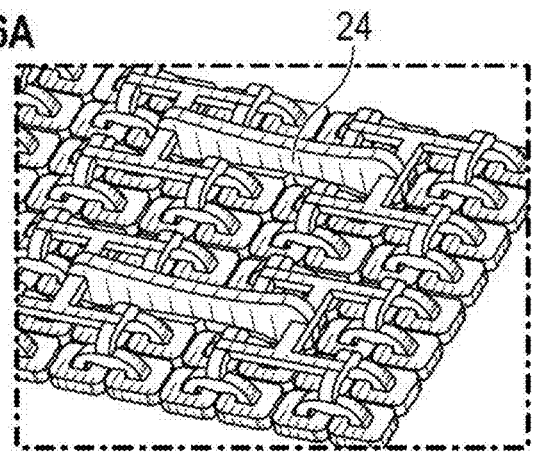
Figure 6D:
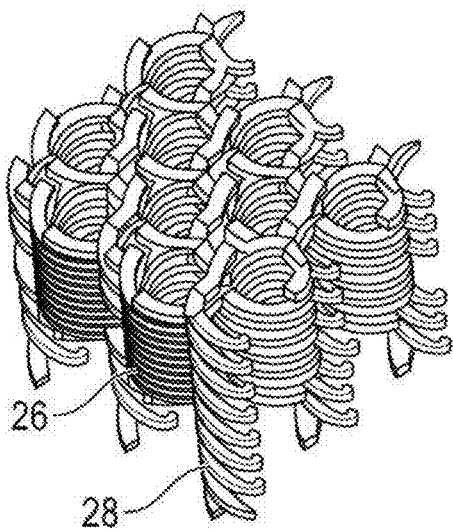
Figure 6E:
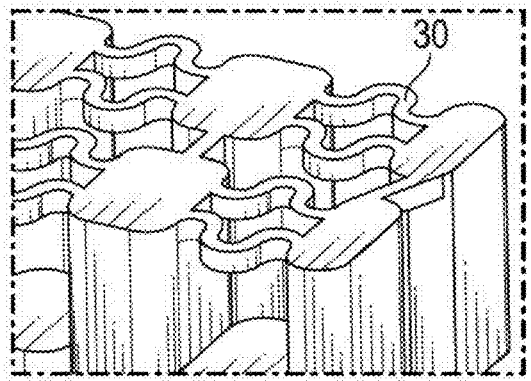

As illustrated in FIG. 6A, adjacent segments 12 of one type of embodiment are joined to different elements of nested coils, allowing relative translation, but preventing lateral separation of segments 12. As illustrated in FIG. 6B, adjacent segments 12 of another type of embodiment are joined by pin-slot features 22 that again allow relative translation but prevent lateral separation of segments 12. As illustrated in FIG. 6C, adjacent segments 12 of another type of embodiment are joined by a grid of torsion bars 24 that also help balance the load across the implant surface. As illustrated in FIG. 6D, adjacent segments 12 of another type of embodiment include small-diameter coils 26 linked by larger-diameter coils 28 to form an implant surface, as illustrated in more detail in FIGS. 17A-17C. As illustrated in FIG. 6E, adjacent segments 12 of another type of embodiment are joined by compliant flexures 30.

Figure 7A:
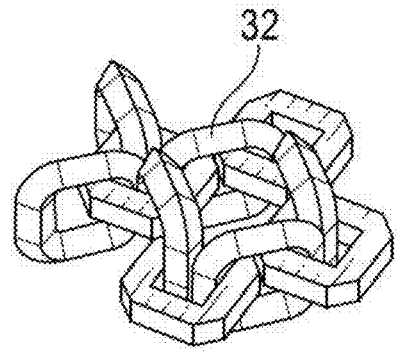
FIGS. 7A-7F show perspective views of various methods for interlocking segments of an implant.
Figure 7B:
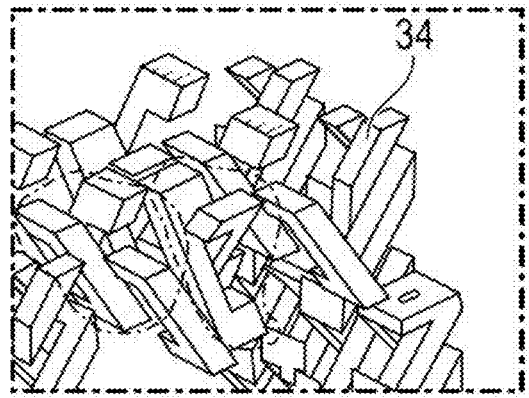
Figure 7C:
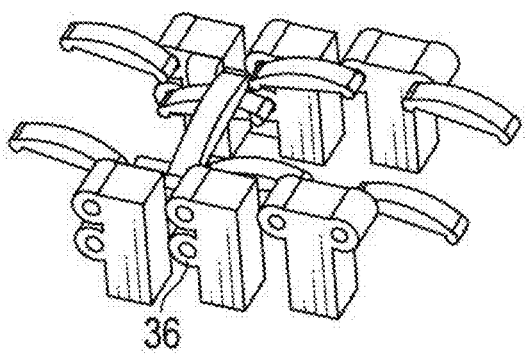
Figure 7D:
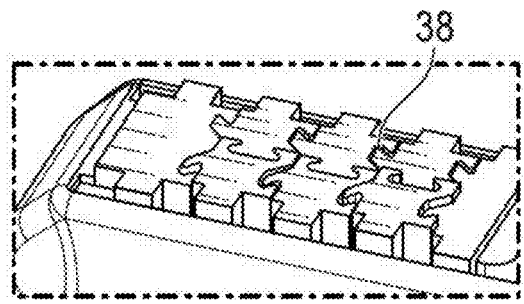
Figure 7E:
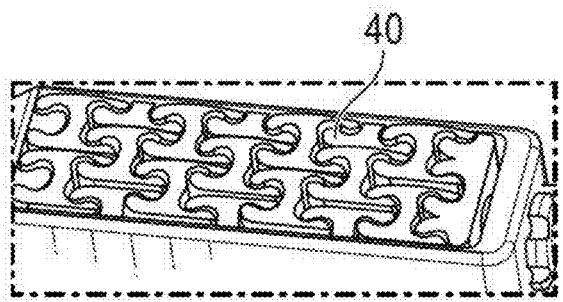
Figure 7F:
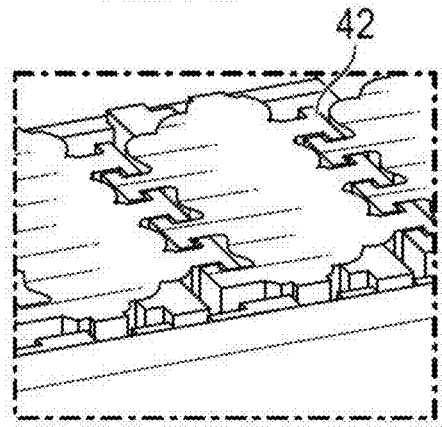

FIGS. 7A-7F illustrate various alternative illustrative embodiments of manners in which adjacent segments 12 may be made interlocking while providing a certain amount of sliding motion relative to each other in a generally superior-inferior direction. FIG. 7A illustrates one way in which a surface of the implant 10 may be formed of interlocking chain mail links 32 in some embodiments. FIG. 7B illustrates one way in which segments 12 may be formed to have interlocked bars 34 in certain embodiments. FIG. 7C illustrates one way in which adjacent segments 12 may have articulating joints 36 in some embodiments. FIG. 7D illustrates one manner in which adjacent segments 12 may be formed with dovetail joints 38 in some embodiments. FIG. 7E illustrates one way in which adjacent segments 12 may be formed with interlocking shapes 40 in certain embodiments. FIG. 7F illustrates on manner in which adjacent segments 12 may be formed with corresponding T-slots 42.

As discussed previously, prior expandable interbody implants cannot conform effectively because they typically have a single lift mechanism (e.g., a ramp, a wedge, or the like) that performs all the lifting at a single point. Embodiments of the present invention, however, provide lifting at multiple points to achieve conformance with the shape of the vertebral endplates. In certain embodiments of the invention, the lift mechanism is configured to apply equal lift force or bone contact pressure at all segments 12.

In certain embodiments, the lift mechanism includes an inflatable balloon or bladder (similar to a kyphoplasty balloon) temporarily or permanently disposed within a central cavity of the implant. After the implant 10 is placed in the vertebral space, the inflatable balloon or bladder is inflated until the segments 12 contact the endplates of the vertebrae, and additional inflation may be provided to achieve additional height and/or lordosis. Then, the adjustment of the segments 12 is locked, such as using one of the methods discussed herein, and the balloon or bladder may be deflated and potentially removed from the implant.

Figure 8A:
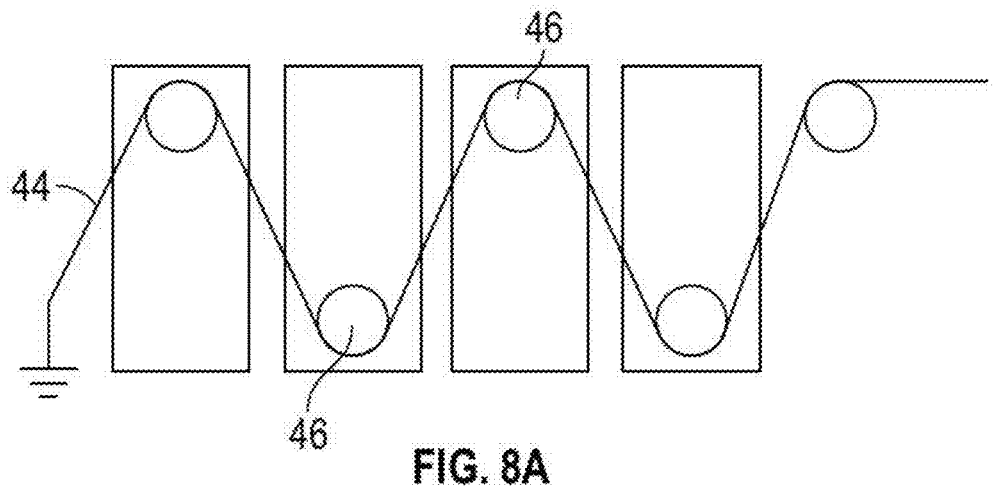
FIGS. 8A and 8B show manners to expand an implant.
Figure 8B:
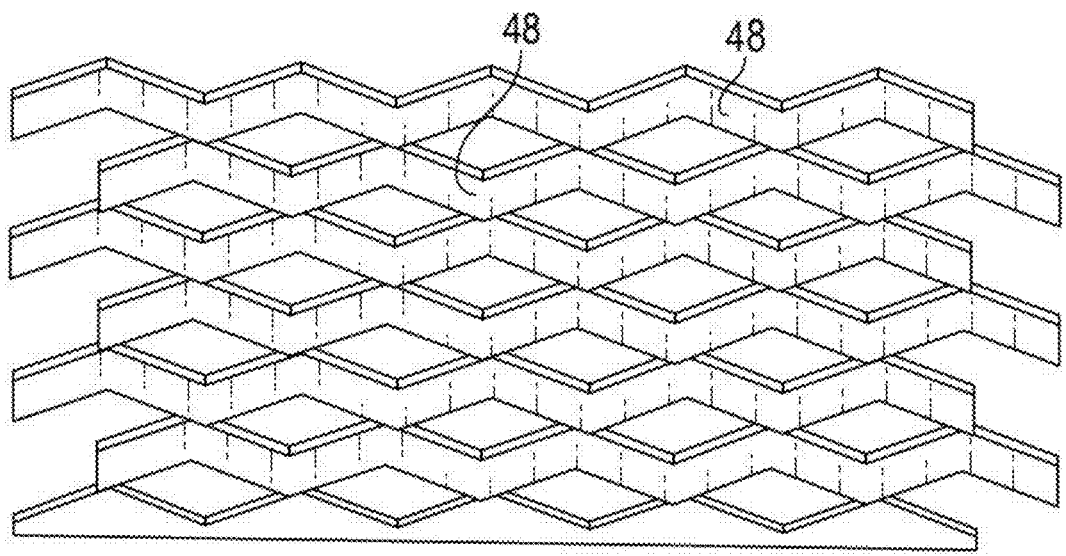

FIGS. 8A and 8B illustrate alternate methods for providing distributed lifting to segments 12 of embodiments of the implant 10. According to the method illustrated in FIG. 8A, a tension wire, such as a nitinol wire 44 acts on pulleys 46 on opposite-facing segments 12, such that the segments 12 can lift with equal force per segment 12. In another type of embodiment, illustrated in FIG. 8B, the implant 10 is built up from corrugated layers 48, where each layer 48 is allowed to conform by being springy. In such embodiments, a collapsed height is achieved when alternating layers are shifted and allowed to nest, and a raised height is achieved by shifting the alternating layers to an offset position such as is shown in FIG. 8B.

Figure 9A:
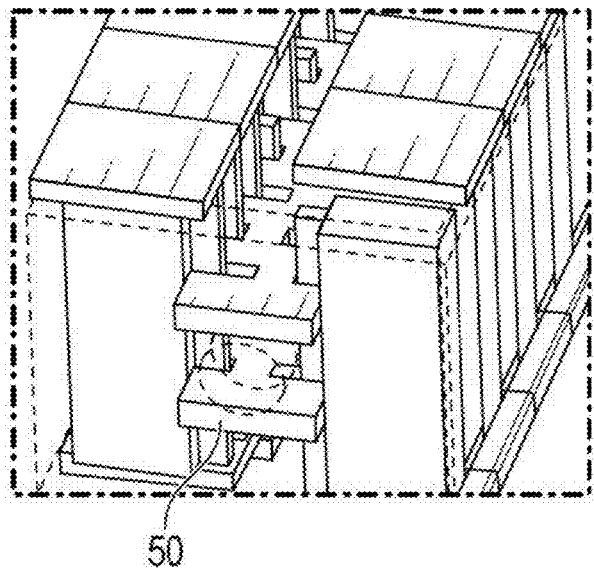
FIGS. 9A-9C show manners to expand an implant.
Figure 9B:
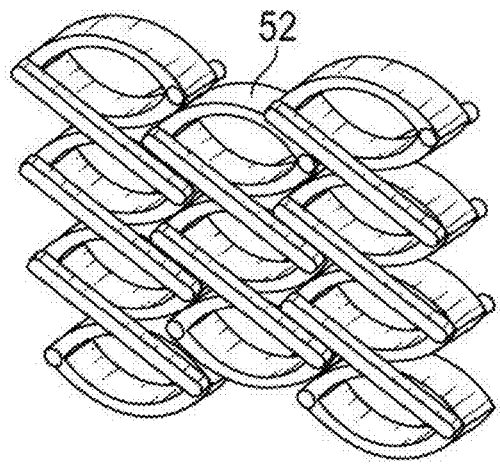

FIGS. 9A-9B illustrate certain alternate methods for providing distributed lifting to the various segments 12 of the implant 10. In embodiments such as illustrated in FIG. 9A, a central plate 50 has slits which pinch on rails on each segment 12. As the central plates 50 are separated, the attached segments 12 move with the central plates 50; however, when the force on any segment 12 exceeds the friction generated by the pinch force (e.g., when that segment 12 contacts the vertebral plate with sufficient force), that segment 12 stops traveling. Other segments continue traveling until a conformed shape and distributed load have been achieved, wherein positions of the segments are locked as previously discussed.

Figure 9C:
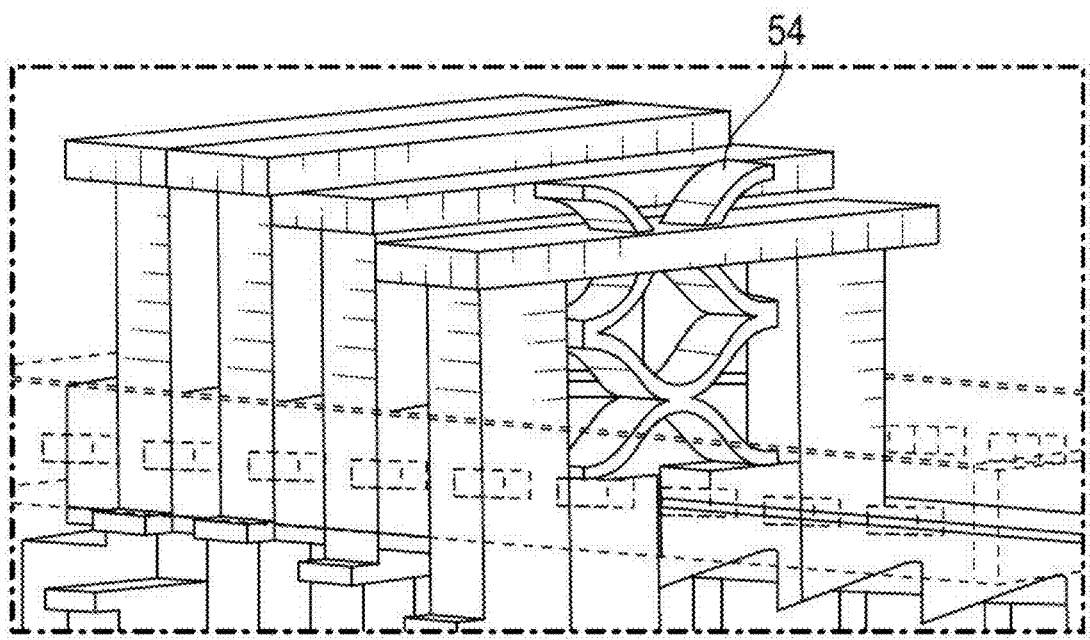

In embodiments such as illustrated in FIG. 9B, stacks of diamond- or almond-shaped springs 52 may be provided in the implant 10. When the springs 52 are forced into each other laterally, they will expand vertically. A single force applied to the end of the stack causes all the stacks to experience an expansion and lift. In embodiments such as illustrated in FIG. 9C, each segment 12 may be provided with its own spring 54 to lift it into contact with the bone of the vertebral endplate. In some such embodiments, the segments 12 are held in a retracted position, compressing the springs 54, until the implant 10 is in a desired position, after which the segments 12 can be released to allow the springs 54 to cause the segments to expand and lift, thereby conforming to the vertebral endplates.

Figure 10:
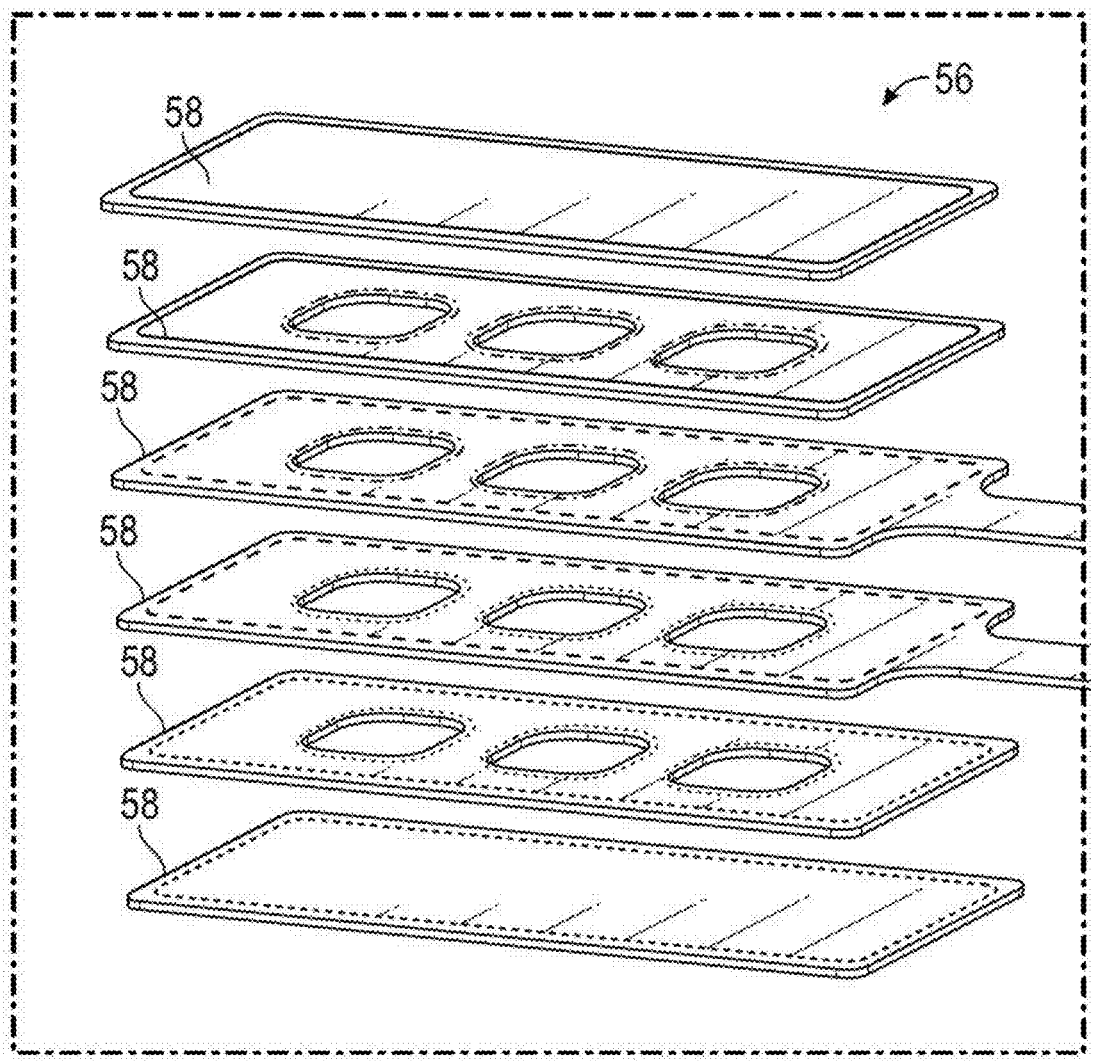
FIG. 10 shows an exploded view of a representative bladder.

FIG. 10 illustrates in exploded view one embodiment of a shape-controlled bladder or balloon (hereafter bladder 56) adapted to provide lift or separation to the segments 12 of the implant 10. In this and similar embodiments, the bladder 56 is formed of multiple layers that allow the bladder 56 to expand vertically (in the superior-inferior direction) while self-constraining against unwanted lateral expansion, which would put unnecessary loads on the frame 14. Kyphoplasty balloons tend to expand equally in all directions, but for an expanding interbody implant, it would be more desirable for the bladder 56 to only (or largely only) expand vertically. In the illustrated embodiment, the bladder 56 is formed of various layers that are bonded on alternate edges (inner and outer edges) to form a bellows-like construction, and the layers have internal reinforcement that prevents or reduces lateral expansion. In alternate embodiments, other internal reinforcements prevent or minimize lateral expansion.

Initially, the bladder 56 is sized to fit in a flat, rectangular cavity. In some embodiments, the bladder 56 is designed to receive two cycles of inflated pressure of approximately 400 pounds per square inch (psi) (approximately 2,800 kilopascals (kPa)) for five minutes each, or approximately 200 psi (approximately 1,400 kPa) for one hour. The bladder 56 of some embodiments is flexible enough to be removed from an approximately 0.150 inch to approximately 0.170 inch (approximately 3.81 to approximately 4.32 mm) hole. The dimensions of the cavity will vary based on implant footprint and height, but in one illustrative embodiment, the cavity has dimensions approximately as follows (prior to inflation of the bladder 56): a length of approximately 0.743 inches (approximately 18.9 mm), a width of approximately 0.308 inches (approximately 7.82 mm), and a height of approximately 0.036 inches (approximately 0.914 mm). The access hole for the implant 10 in this illustrative embodiment may be approximately 0.170 inches in diameter (approximately 4.32 mm in diameter), and a feed tube for the bladder 56 may be approximately 0.105 inches in diameter (approximately 2.67 mm in diameter).

Figure 11:
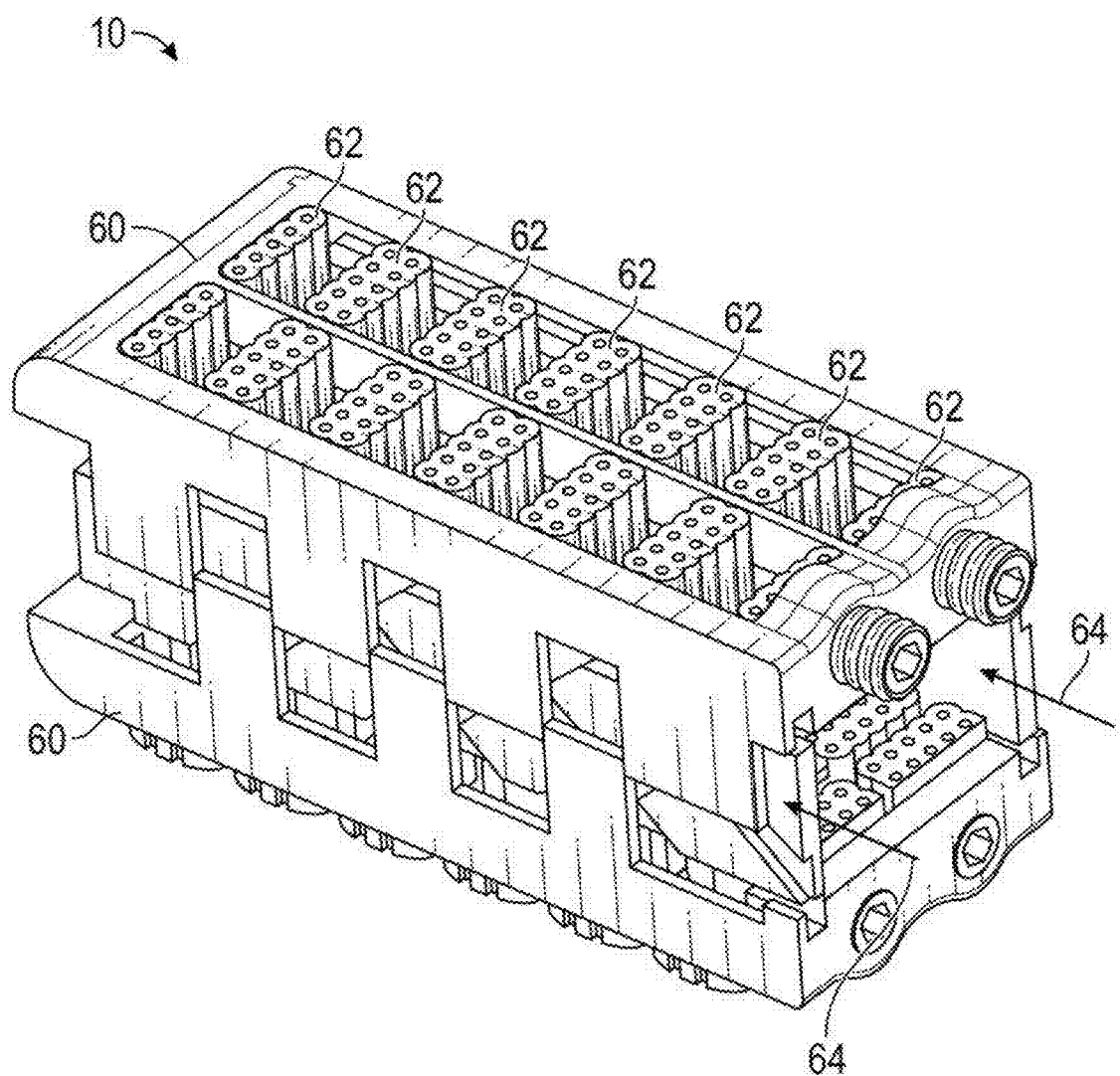
FIG. 11 shows a perspective view of a portion of an implant.
Figure 12:
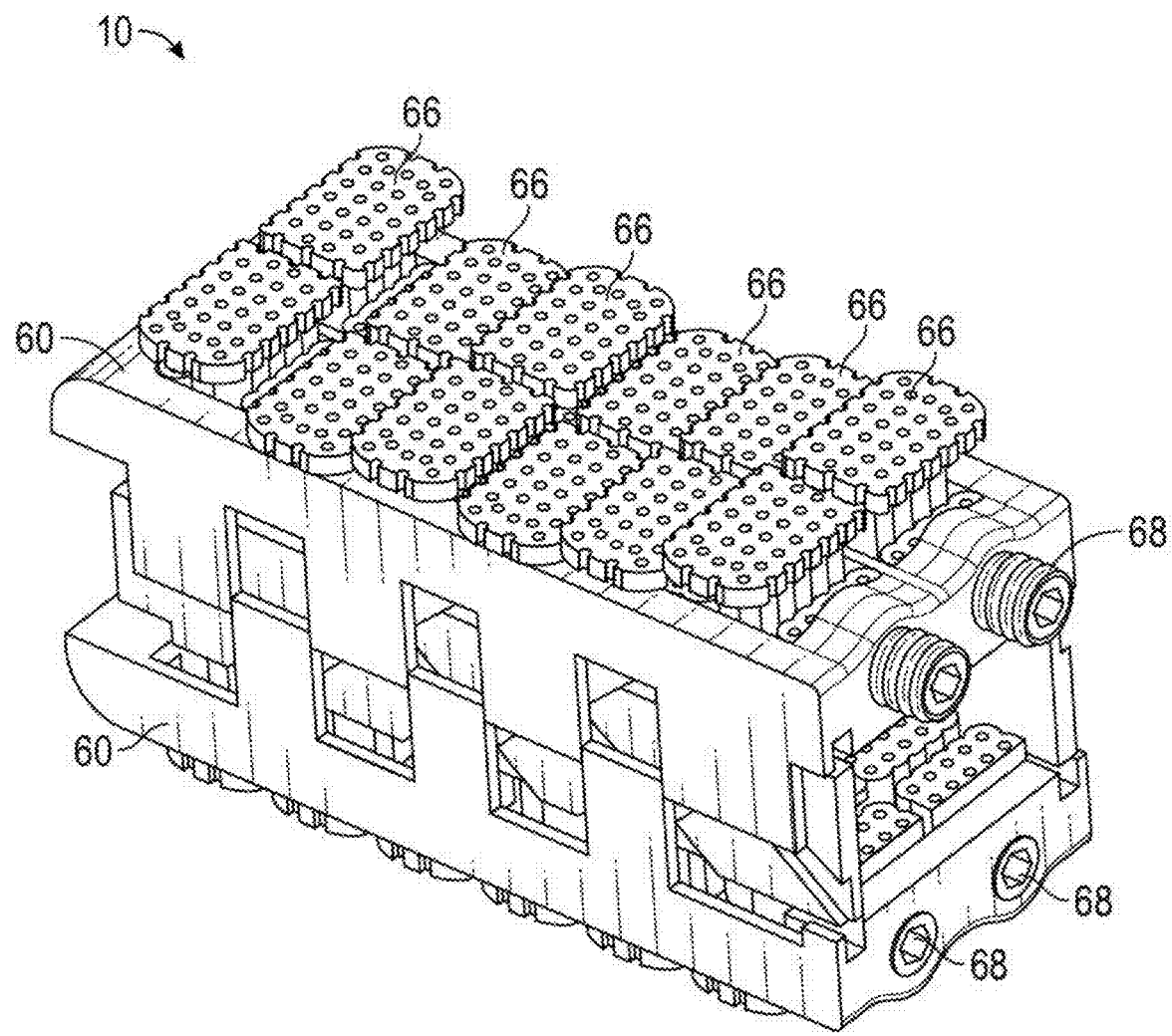
FIG. 12 shows a perspective view of an implant.
Figure 13:
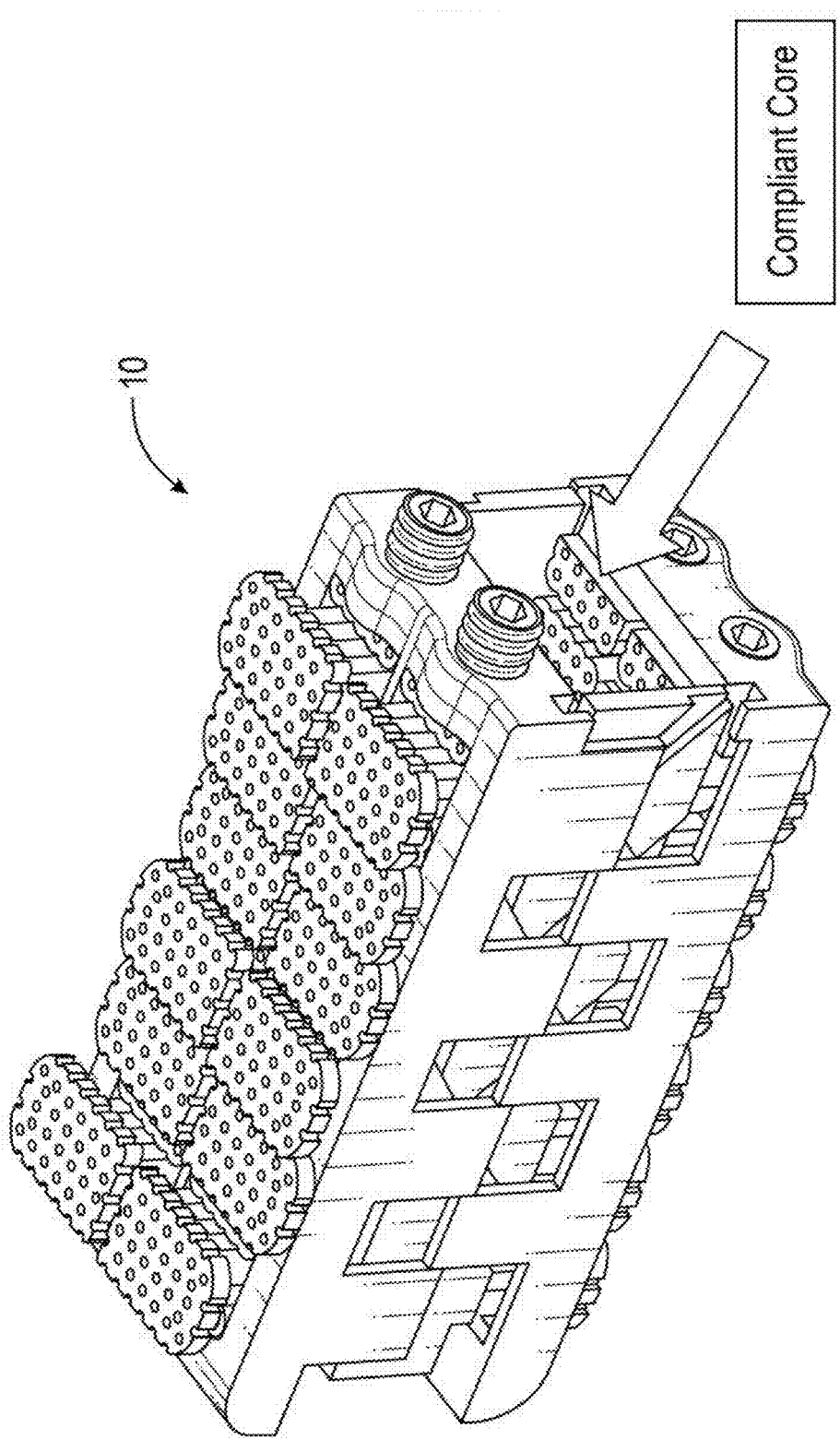
FIG. 13 shows a perspective view of an implant.

In some embodiments, the implant 10 is configured to provide an adjustable base height for the implant, with conformability at a selected height. An example of such an embodiment is illustrated at FIGS. 11-13. FIG. 11 shows that the embodiment of the implant includes two frame halves 60. Each frame half 60 carries a set of static blocks 62 which move with the frame half 60 in superior/inferior direction, but are able to slide laterally in the frame half 60. The implant 10 also includes height bars 64 that include ramps that interact with ramps on the frame halves to increase and/or measure the base height of the implant 10.

FIG. 12 shows additional components of the implant assembly, namely moving blocks 66. The internal bladder 56 (not shown) causes the moving blocks 66 to conform to the vertebral endplates. The internal bladder 46 may also contribute to the force causing the increase in the base height of the implant. Once conformity to the endplate has been achieved, end screws 68 are tightened to compress the static and moving blocks together and lock the conformed shape. Thereafter, the bladder 56 may be removed and replaced with a compliant core, as illustrated in FIG. 13. In some embodiments, the height bars 64 may be released to allow the implant 10 to settle onto the compliant core (e.g., the static blocks 62 rest on the compliant core and transfer forces therethrough).

Figure 14A:
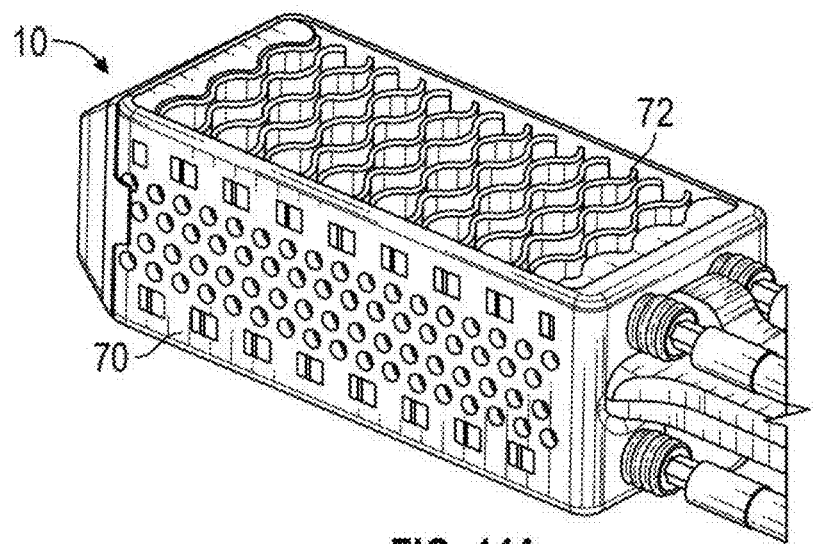
FIGS. 14A-14C show perspective views of an implant.
Figure 14B:
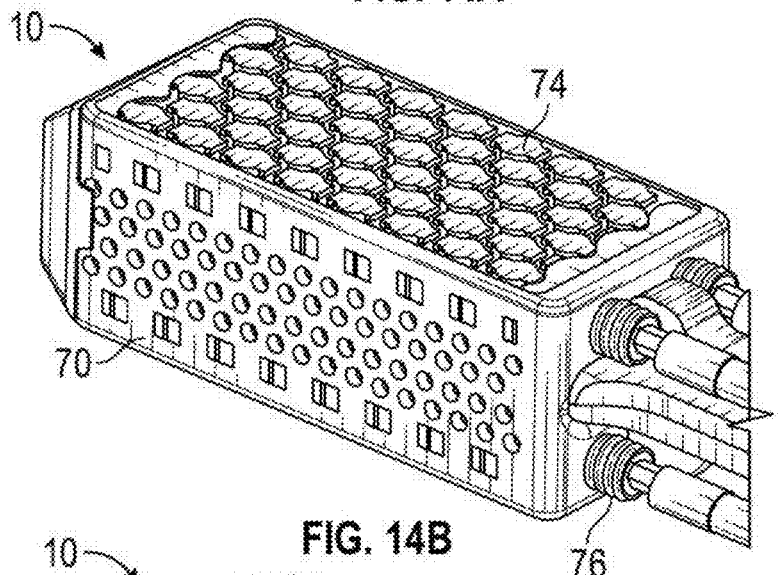
Figure 14C:
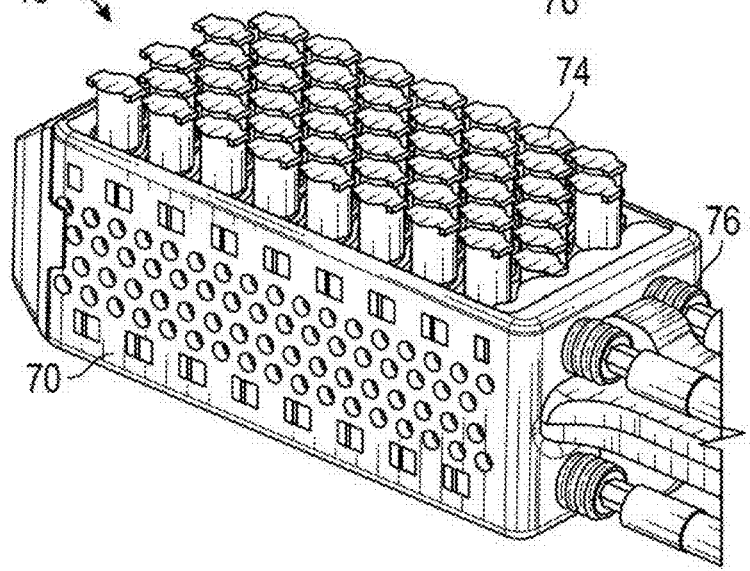

FIGS. 14A-14C illustrate another type of embodiment of the implant 10, this embodiment being a multi-piston embodiment that has a compliant/porous frame 70. The frame 70 is fitted with multiple cross-members 72, as illustrated in FIG. 14A. The cross members 72 are able to translate a short distance laterally within the frame 70. The implant 10 also includes displacement-limited pistons 74 between the cross members 72. The bladder 56 (not shown) is inserted between the upper and lower layers of pistons 74. Under pressure from the bladder 56, the pistons 74 move outward to conform to the vertebral endplate and provide a distraction force, as illustrated in FIG. 14C. (FIG. 14C does not illustrate movement of the lower pistons 74, but such pistons 74 would be present and move as well.) Once movement of the pistons 74 is complete and to be locked, screws 76 (or some other mechanism) may be actuated to compress the cross members 72 and pistons 74 to frictionally lock the conformed shape and height. The inserter tool and bladder 56 are removed and the implant 10 is post-packed with bone graft material, etc., if desired.

Figure 15A:
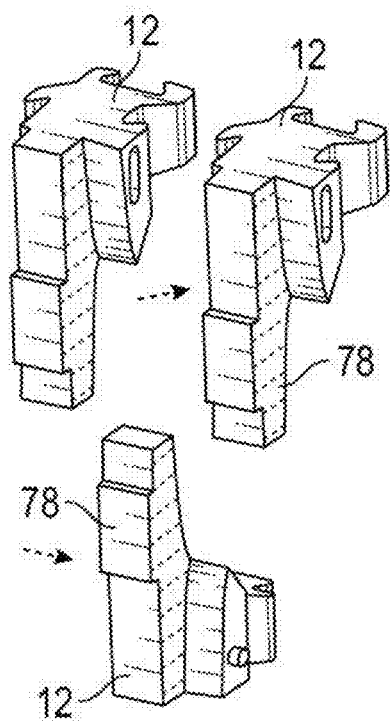
FIGS. 15A-15C show perspective views of implants and components of implants.
Figure 15B:
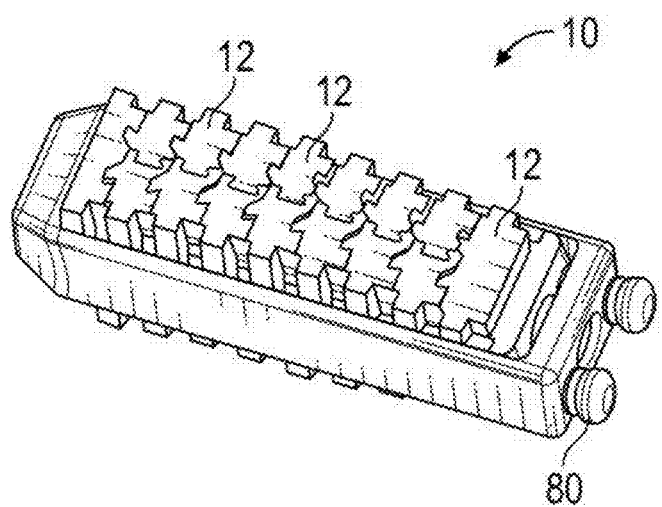
Figure 15C:
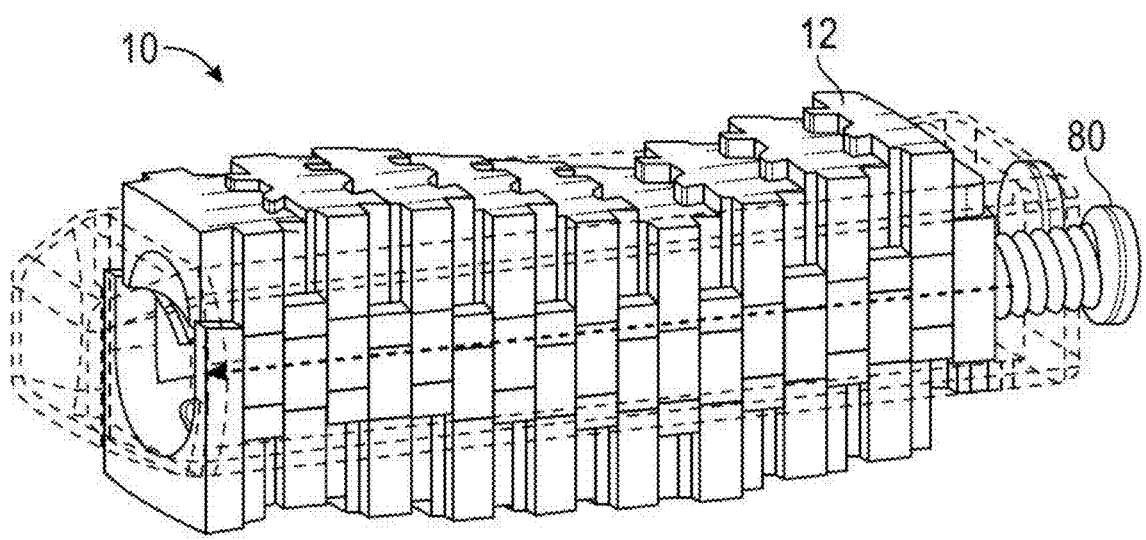

In additional embodiments, the implant 10 includes multiple compliant segments 12 supported by fingers 78, as illustrated in FIG. 15A. The fingers 78 of upper segments 12 slide on fingers 78 of lower segments 12 on adjacent surfaces. Multiple segments 12 lock together in a full implant, as shown in FIGS. 15B and 15C (illustrating varying embodiments of the implant 10). During implantation, the bladder 56 causes the segments 12 of the implant 10 to assume the conformed shape and provides a distraction force. Then, screws 80 or some other locking mechanism is actuated to compress all fingers 78 together (e.g., through the lateral load path illustrated in FIG. 15C) to frictionally lock the fingers 78 and thus the segments 12 together to maintain the conformed shape and height. The bladder 56 is removed and post packing occurs, if desired.

In alternate embodiments of the implant, something other than the bladder 56 is used as a lift mechanism. In some embodiments, a central area of the implant 10 is filled with a biocompatible but extremely hydrophilic material. After implantation, a saline solution is applied to the hydrophilic material such that the material swells at a certain pressure to cause the segments 12 of the implant to conform and lift in a manner similar to the manners illustrated and described herein.

Figure 16D:
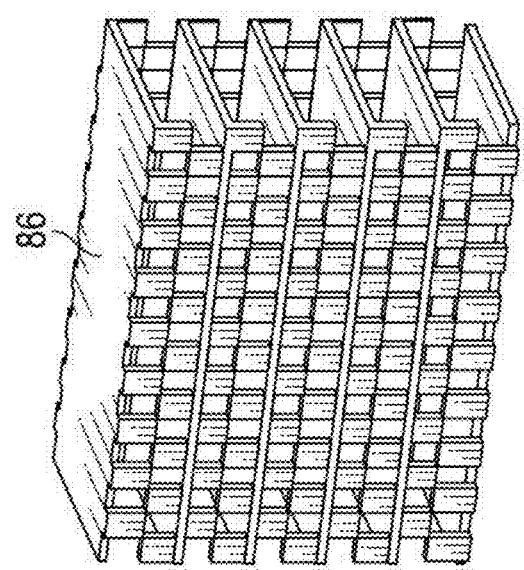
FIGS. 16A-16D illustrate methods for expanding segments of an implant.
Figure 16B:
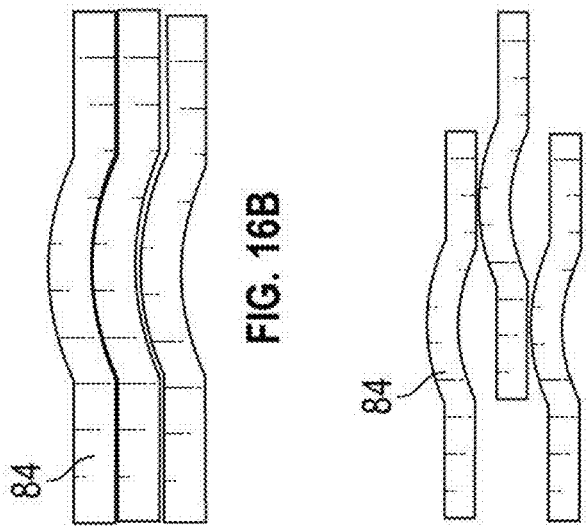
Figure 16C:
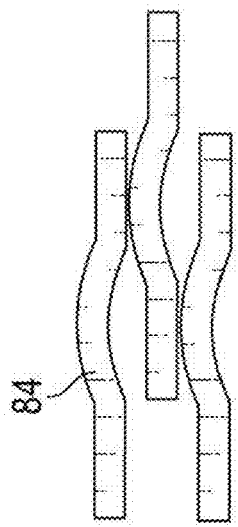
Figure 16A:
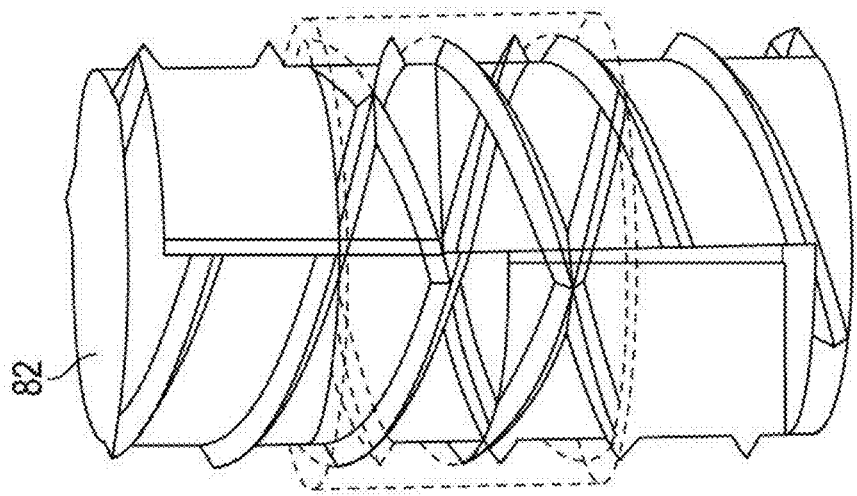

FIGS. 16A-16C illustrate other mechanisms that may be used with embodiments of the invention. FIG. 16A illustrates a threaded cylinder segment 82 with portions containing a right-hand thread and other portions containing a left-hand thread. A simple rotation causes the cylinder segment 82 to simultaneously apply upward and downward forces, and can also cause locking. Multiple instances of the cylinder segment 82 would be used in each implant 10.

FIGS. 16B-16D illustrate how dimpled moveable layers 84 can be interleaved and nested then translated relative to each other to provide height control. By selecting and zoning the location of dimples to different areas of the moveable layers 84, the implant 10 may be provided with height control of left/right as well as anterior/posterior areas of the implant 10 as the surgeon may desire during implantation. Static layers 86 of the implant 10 may be toothed together, as illustrated in FIG. 16D to preserve the implant footprint across variations in implant height.

FIGS. 17A-17C illustrate an example of embodiments in which interlocking coils form the conforming surfaces of the implant 10. In this type of embodiment, interlocking small-diameter coils 26 and large-diameter coils 28 are created in upper sets 88 and lower sets 90. The upper sets 88 and the lower sets 90 are located in a dual-slot frame 92, with the small-diameter coils 26 of the upper sets 88 interdigitated with the small-diameter coils 26 of the lower sets 90. The implant 10 is inserted while in the position shown in FIG. 17A, then the upper sets 88 and the lower sets 90 are expanded in a fashion similar to that disclosed herein, and the height is locked by compressing (laterally) the interdigitated smaller-diameter coils 26, as shown in FIG. 17B. FIG.

17C shows the interlocking coils in more detail. The interlocking coils can be extended in their conformability by not typing the multiple leads of the same coils together, which leads to multiple nested structures which each have their own compliance and can translate on each other.

FIG. 18A illustrates how in some embodiments, a coil structure 94 could be disposed laterally instead of vertically (as illustrated in FIGS. 17A-17C) to create a conformable surface. FIG. 18B illustrates that in some embodiments, an implant 10 includes a plurality of rings 96 tuned to have a correct stiffness. FIG. 18C illustrates that where a ramp mechanism 98 is used to cause height increases of the implant 10 (thereby reducing the inventory/carrying cost for carrying implants of varying height), and where space does not permit the ramp mechanism 98 to give the implant full height in a single stroke, shims 100 can be inserted between strokes to increase the height variability of the implant 10.

Figure 19:
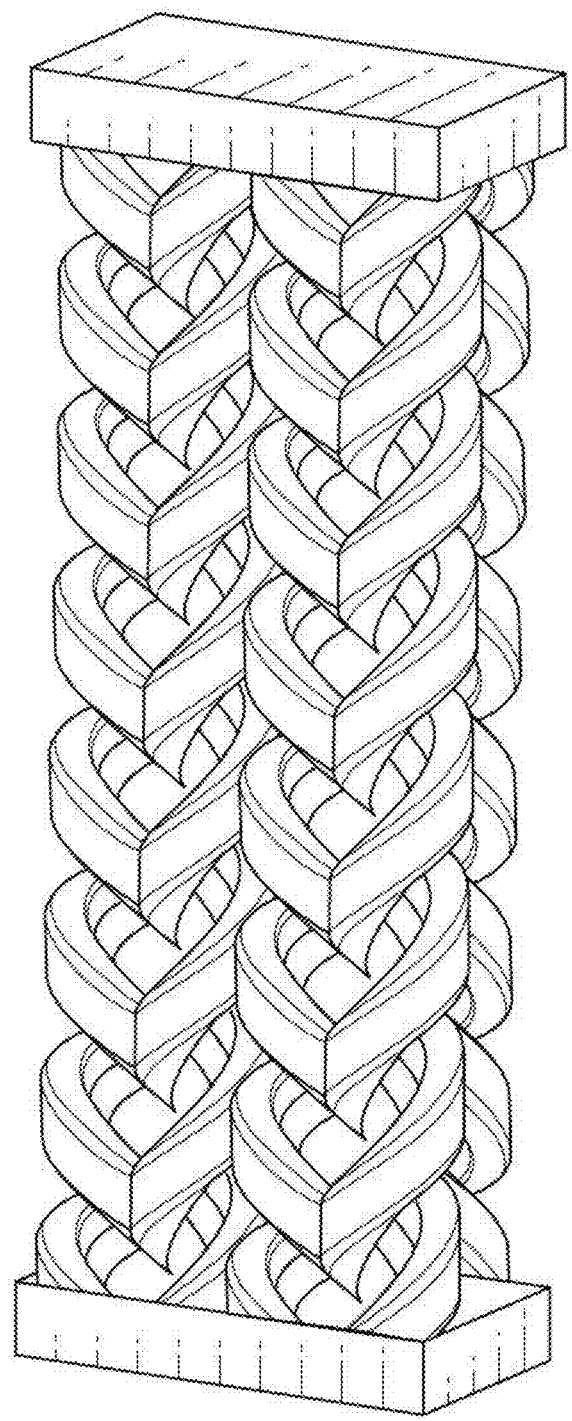
FIG. 19 illustrates one construction of a block of an implant.

FIG. 19 illustrates one manner of constructing the compliant blocks of the embodiments illustrated in FIGS. 11-13. The manner of constructing illustrated in FIG. 19 may be used for both the static blocks 62 and the moving blocks 66. The construction method uses multiple nested coils as described in U.S. Patent Application Publication No. 2017/0156880 to Halverson and Hawkes, published on Jun. 8, 2017, which is incorporated herein by reference for all it discloses. The diameter of the nested coil structure illustrated in FIG. 19 may be smaller than that disclosed in the prior publication so as to improve spatial density and coil stability in a small structure.

Figure 20A:
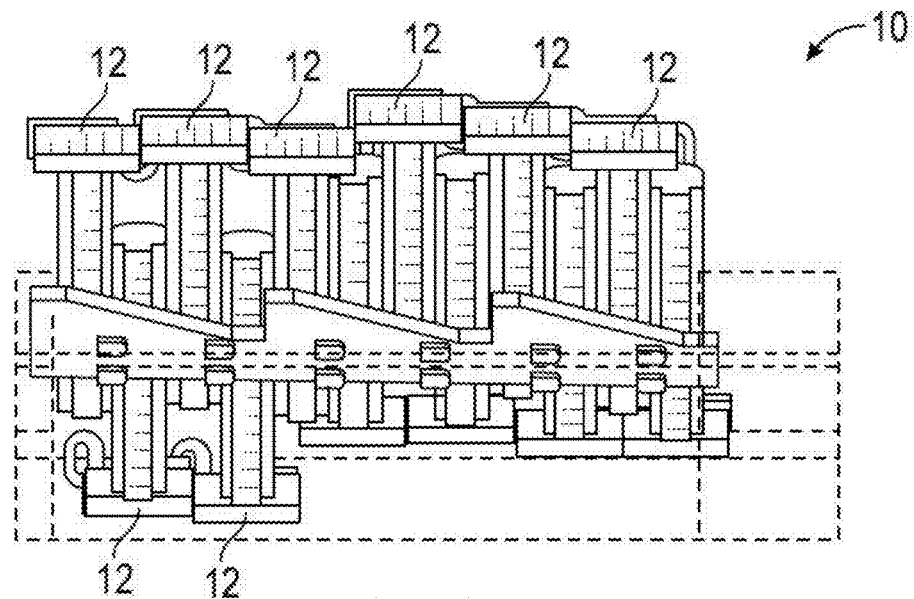
FIGS. 20A-20D illustrate implants and components thereof.

FIG. 20A illustrates an alternate type of embodiment of the implant 10. In this type of implant 10, the stack of segments 12 is lightly loaded with a clamping force. The lifting mechanism incrementally lifts each segment 12 to a given height, then the lifting mechanism is withdrawn. Any segments 12 experiencing a load greater than the frictional force exerted by the initial clamping mechanism will then retreat until other segments 12 come into contact with the bone and the load is evenly distributed over the segments 12. The clamping force is then increased to a final value to fix the shape and height of the implant 10 and its segments 12. Post packing of bone graft material, etc., may then occur as desired.

Figure 20B:
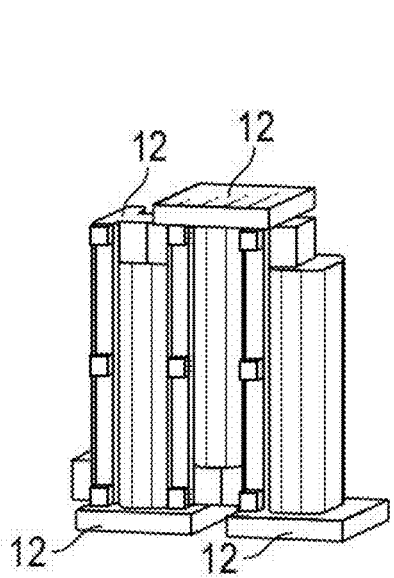
Figure 20C:
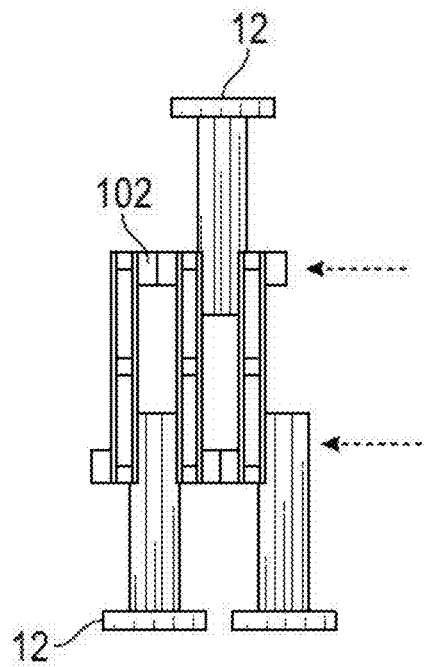
Figure 20D:
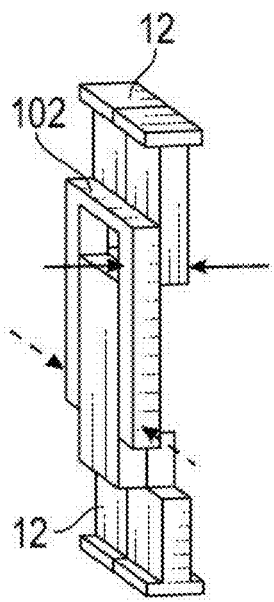

FIGS. 20B-20D illustrate another type of embodiment, in which interdigitation is extended with one or more middle layers 102 such that the segments 12 on each side of the implant 10 can move out farther and still be shape locked. In such embodiments, there are two clamping paths, as illustrated by the arrows shown in FIG. 20C. In some embodiments, the clamping paths can be varied in orientation, as illustrated by the arrows of FIG. 20D.

Figure 21A:
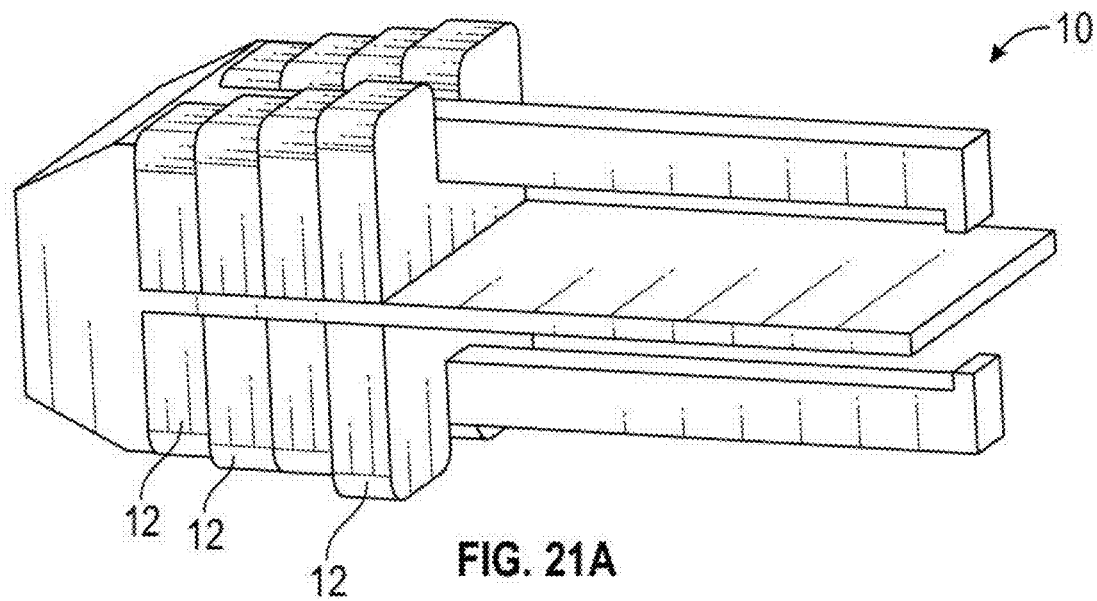
FIGS. 21A-21B illustrate aspects of certain embodiments of an implant.

In some embodiments, a sliding caliper could be used to measure the endplate shape and build a custom implant 10 out of compliant segments of a correct height, as illustrated in FIG. 21A. In some embodiments, a special inserter could be used to assemble the implant 10 in situ, thereby retaining the small-access benefits of the implant 10 being expandable.

Figure 21B:
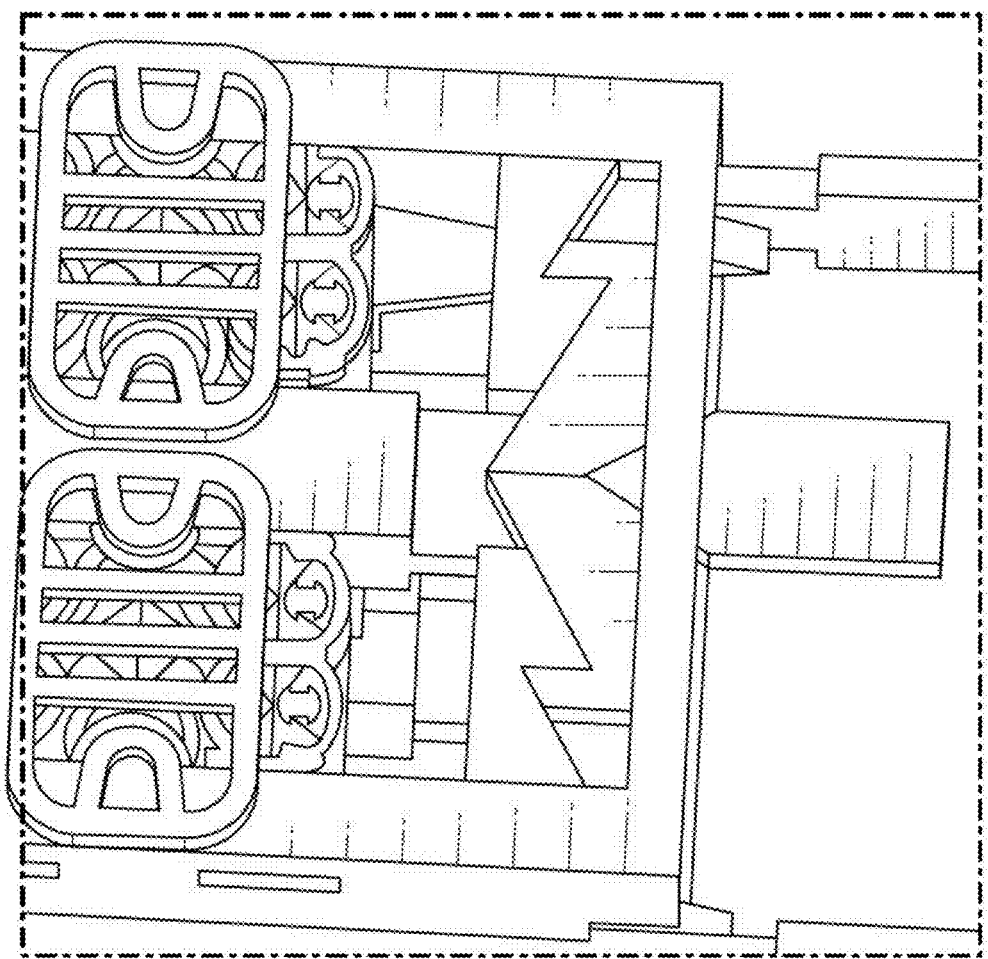

FIG. 21B illustrates that in some embodiments, the screw-based mechanism for locking stacks of blocks or fingers can be replaced with cams, ramps, or wedges.

Figure 22A:
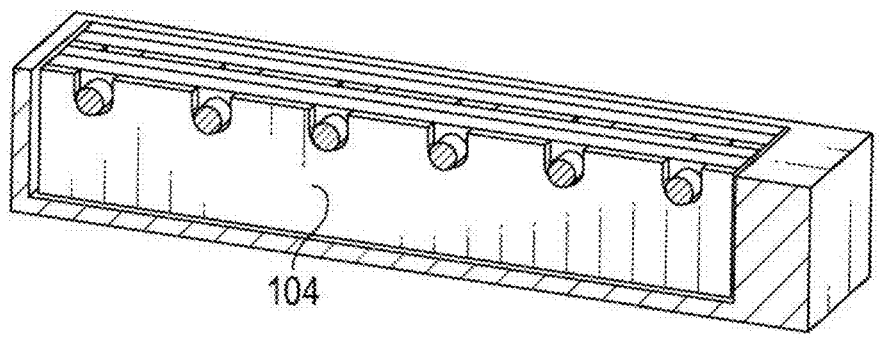
FIGS. 22A-22D illustrate views of an alternate embodiment of an implant.
Figure 22B:
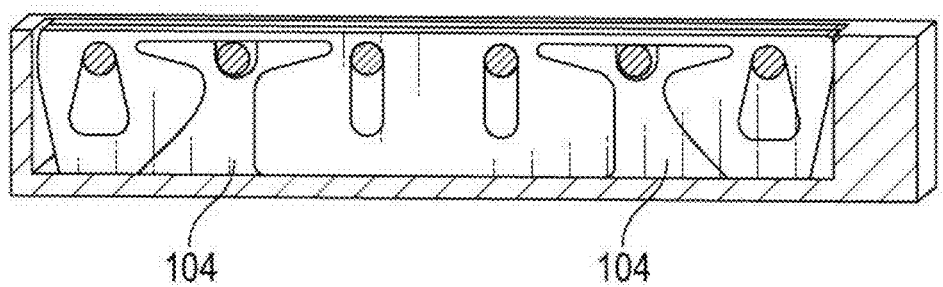
Figure 22C:
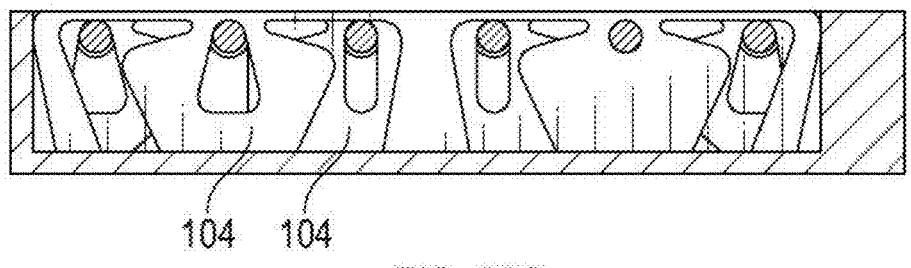
Figure 22D:
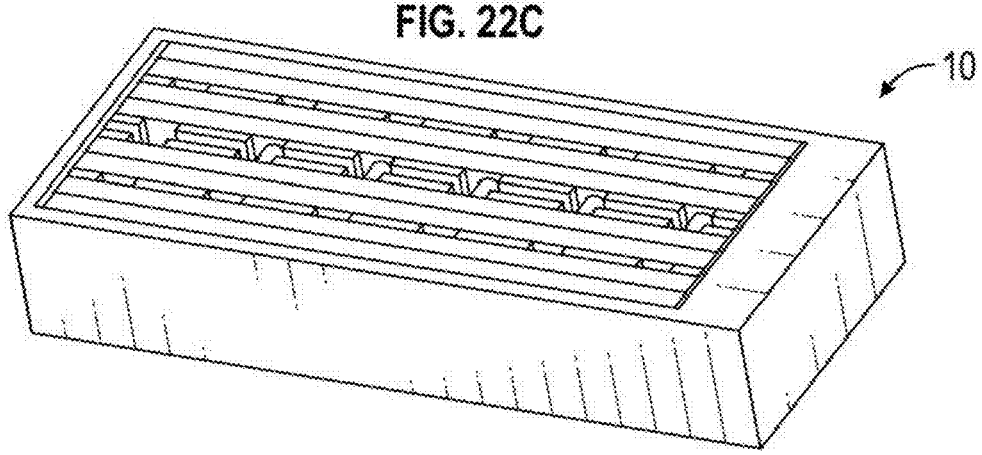

FIGS. 22A-22D illustrate a type of embodiment where the implant 10 is formed of multiple compliant layers 104 that clamp against each other and against a ground layer to maintain an arched/bridged/conformed shape. FIGS. 22A-22C each illustrate a configuration of alternate layers 104, and FIG. 22D illustrates an embodiment of the assembled implant 10.

Figure 23A:
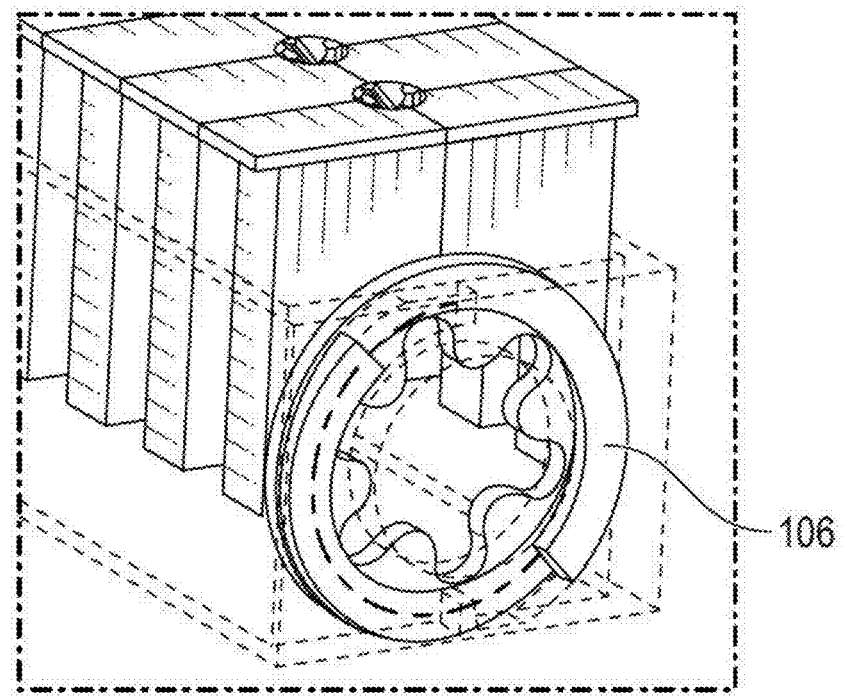
FIGS. 23A-23C illustrate mechanisms for locking segments of an implant.
Figure 23B:
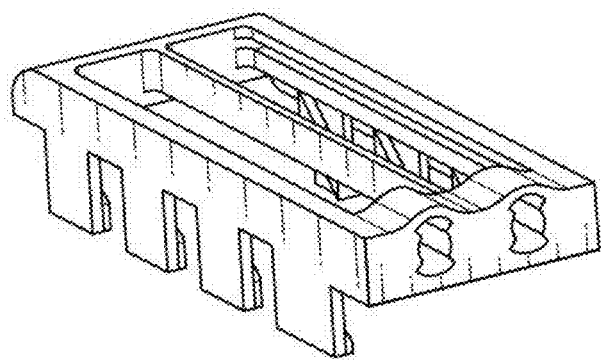
Figure 23C:
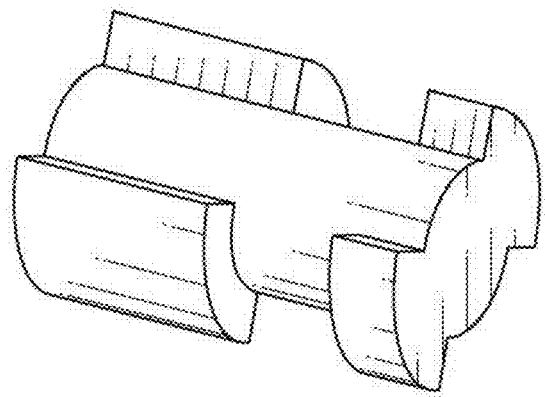

FIGS. 23A-23C illustrate alternate types of clamping mechanisms (other than screws such as end screws 68 or screws 76 or 80) to permit locking of the height of the implant 10. In the illustrative embodiment of FIG. 23A, the implant 10 is provided with a face thread 106 instead of a male-female thread to avoid the radial space loss of the thread overlap area. Such an embodiment provides for a larger driver and better access for the bladder 56 and post packing with graft material than a single male-female thread. The face thread 106 can be left handed on one face and right handed on the other face to reduce the ramp angle of the thread and thus reduce frictional losses. Multiple starts are possible to save space as well.

In some embodiments, as is illustrated in FIGS. 23B and 23C, a conventional threaded locking mechanism can be replaced by a quarter-turn mechanism which always locks to the same kinematic position, thereby saving the surgeon the trouble of worrying that he or she didn't tighten the screws enough or that some factor caused a drive to torque out too early.

Figure 24A:
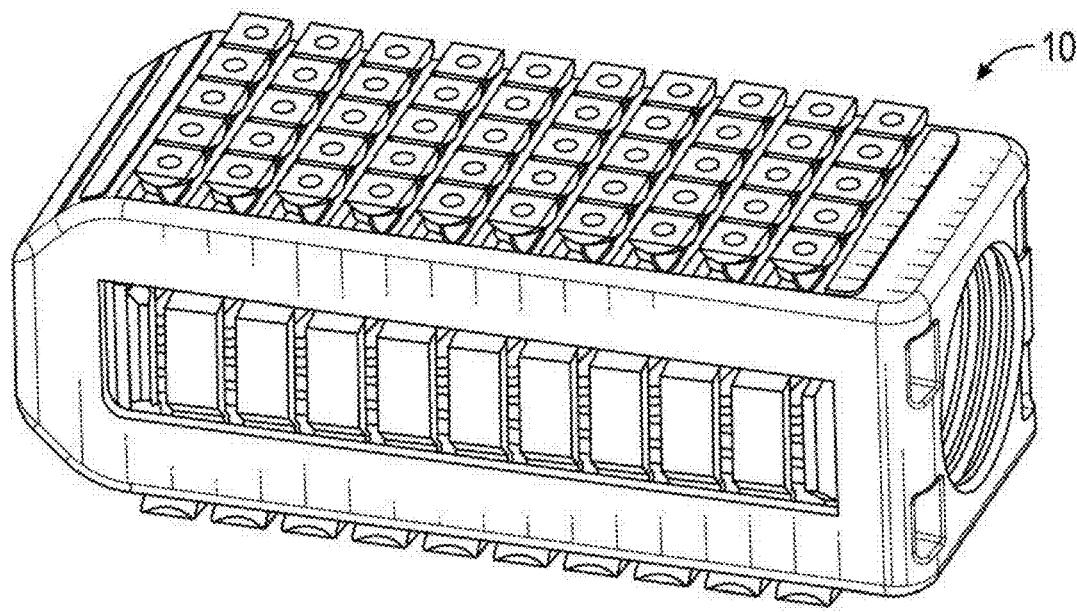
FIGS. 24A-24D illustrate an alternate implant and enlarged views thereof.
Figure 24B:
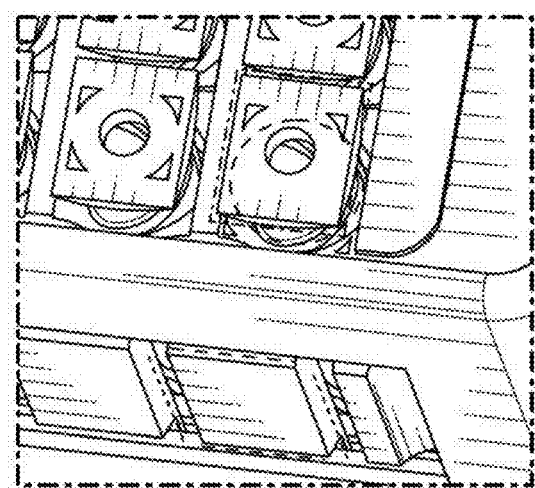
Figure 24D:
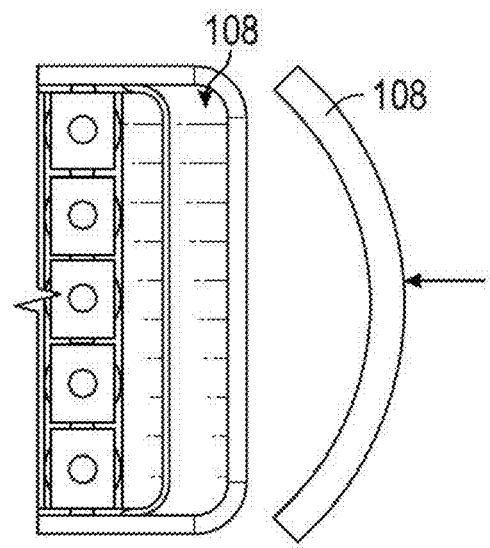
Figure 24C:
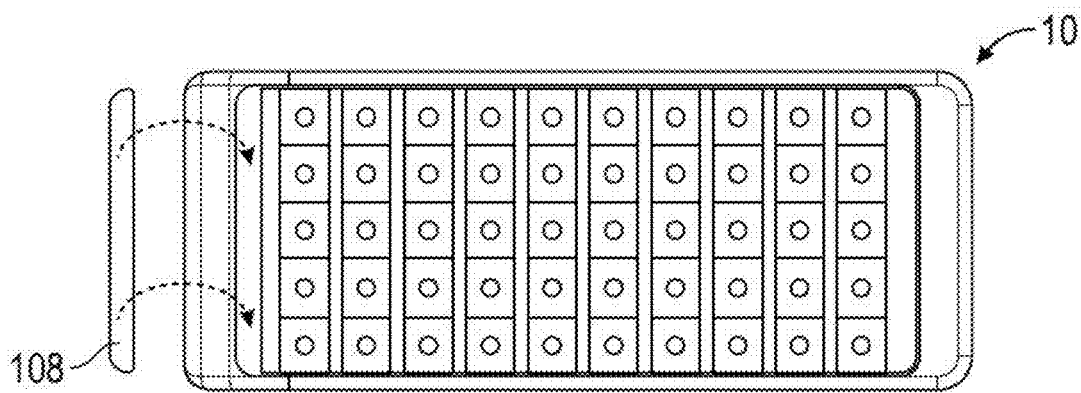

As discussed above, embodiments of the implant may be manufactured using additive manufacturing methods. In such embodiments, clearance between adjacent parts is tuned such that the implant 10 can be manufactured (e.g., printed) as an assembled unit without having adjacent surfaces fuse. FIGS. 24A-24C illustrated considerations that may be used in determining clearances between adjacent parts during fabrication. FIG. 24A shows an embodiment of the implant 10. FIG. 24B shows a close-up view of the implant 10 of FIG. 24A, showing that clearance will be considered between a segment 12 and its containing pocket between a segment 12 and its adjacent segments 12, between a segment 12 and its containing pocket, between a segment 12 and its adjacent segments 12, between a segment 12 and any travel limiters, between a cross bar and the frame 14 of the implant 10, and between the frame 14 and an end bar. The clearances required may be different at each location.

For improved avoidance of component fusion between adjacent parts during 3D printing, the implant 10 can be designed with a separate end portion 108, as shown in FIG. 24C. The implant 10 is printed without the end plate 108 and with the segments 12 and cross webs spaced out. After support removal, the end plate 108 can be inserted and held in place by mechanical means or by welding or bonding, as also illustrated in FIG. 24C. In some embodiments, the end plate can be fabricated in an inverted or arc shape that comes into a desired planar shape when loaded by the locking mechanism force, thereby distributing load (as illustrated by the arrow) evenly across the back of the segment pack, as illustrated in an exaggerated manner in FIG. 24D.

Figure 25A:
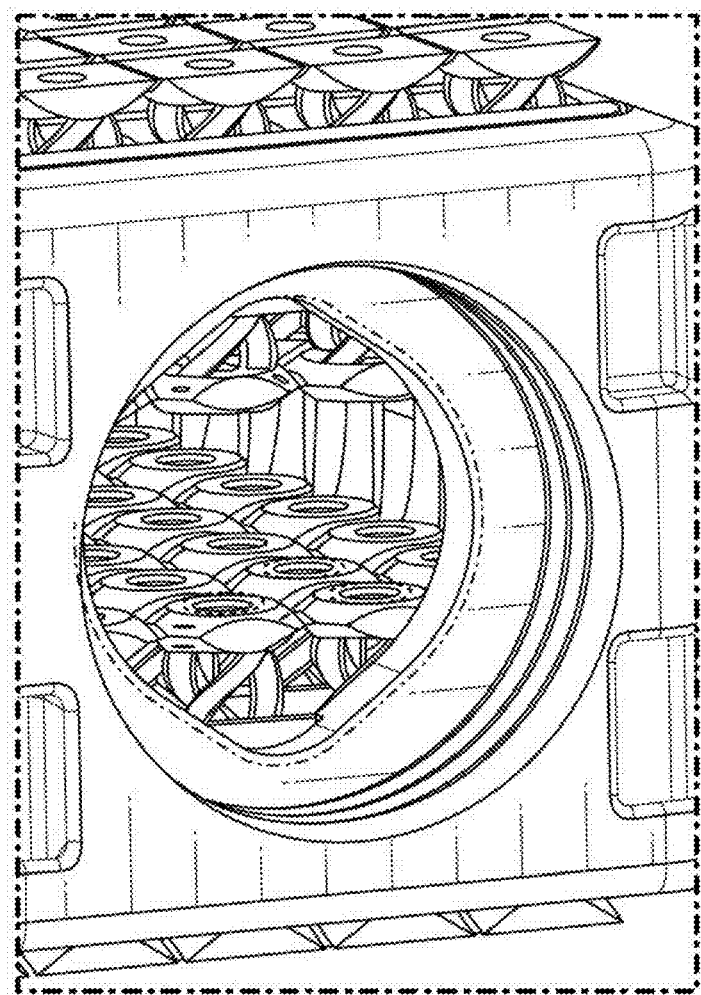
FIGS. 25A and 25B illustrate aspects of an implant.
Figure 25B:
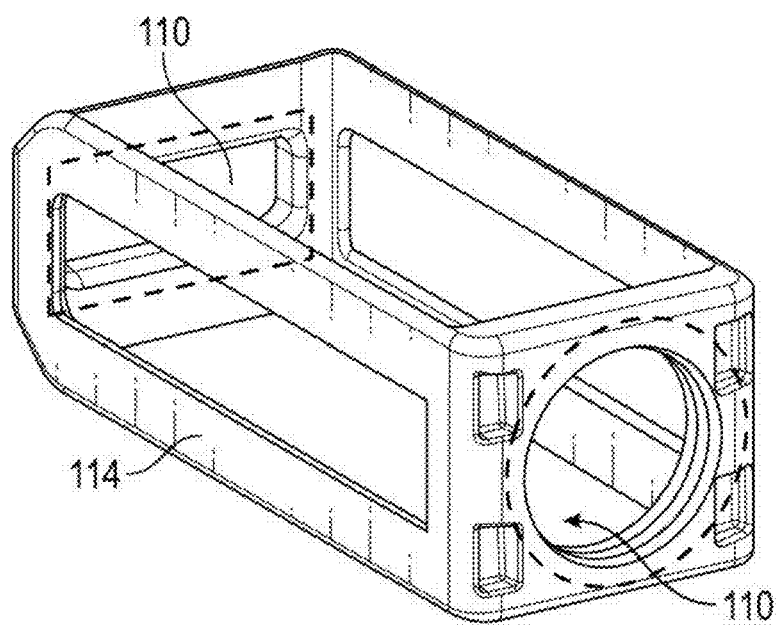

The implant 10 of some embodiments is designed with angled surfaces to facilitate self-supporting 3D printing. The implant 10 of some embodiments is also designed with droop-reducing or droop-compensating features. Additionally, the implant 10 of some embodiments includes segments 12 with minimum-area internal horizontal surfaces to minimize the amount of support material required during 3D printing. These features are illustrated in the view of FIG. 25A. The implant frame 14 of some embodiments, as illustrated in the view of FIG. 25B, has openings 110 at both ends. The openings 110 permit the inner cavity to be accessed from either side, increasing ease of support removal and also make it possible to install the bladder 56 into the inner cavity by a pull-through approach rather than trying to push it in from one end.

Figure 26A:
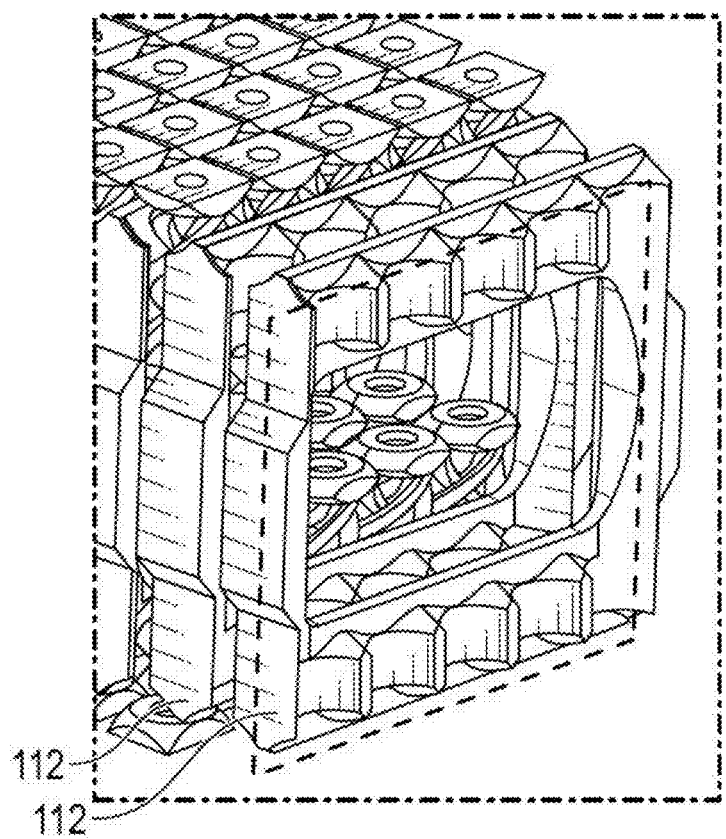
FIGS. 26A and 26B illustrate aspects of an implant.
Figure 26B:
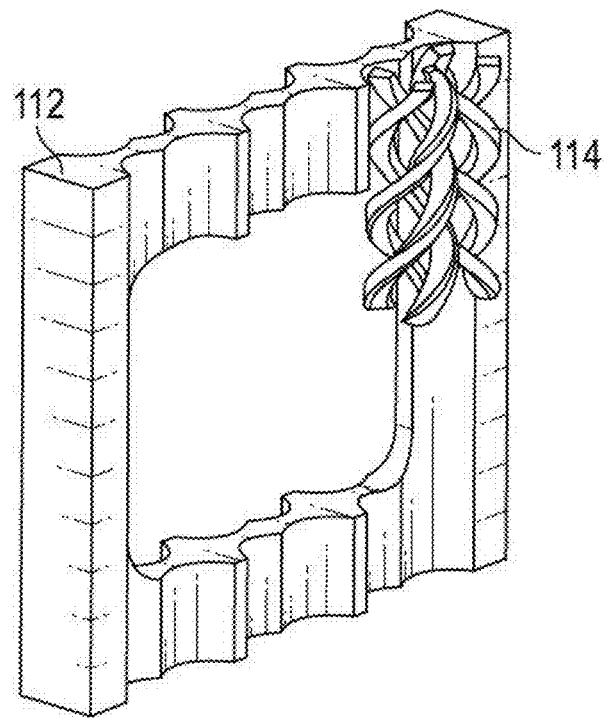

FIGS. 26A and 26B illustrate one embodiment of cross webs 112 used in embodiments of the implant 10 to support the individual segments 12 and to stabilize the segments 12 when compressed to keep the segments 12 at their set heights. The cross webs 112 of this embodiment are planar in nature and have bosses to receive and stabilize the segments. This reduces the stroke required of the locking mechanism. The cross webs 112 are joined top and bottom for direct load transfer in the superior-inferior direction rather than sharing load through the frame 14. In this way, there are no support points on the frame that can slip off. As more-clearly shown in FIG. 26B, coils 114 of some embodiments are grouped in pairs to provide rotational stability without causing excessive loss of shape-matching ability.

Figure 27A:
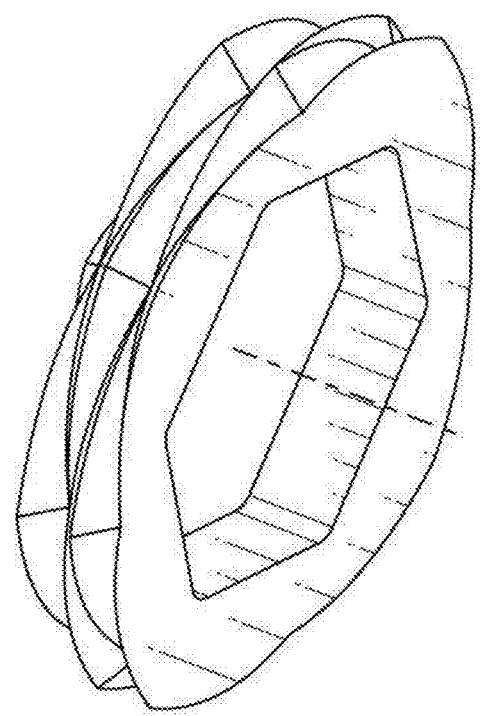
FIGS. 27A and 27B illustrate aspects of an implant and an implant inserter.

In some embodiments, the plate that compresses the segment stack and the frame 14 are each female threaded with a slotted thread such that they can both simultaneously engage a locking screw having both left and right hand threads. This is advantageous in that the required axial length is reduced and the screw (an embodiment of which is illustrated in FIG. 27A) has positive control over the return of the compression plate instead of relying on the spring force of the segment stack.

Figure 27B:
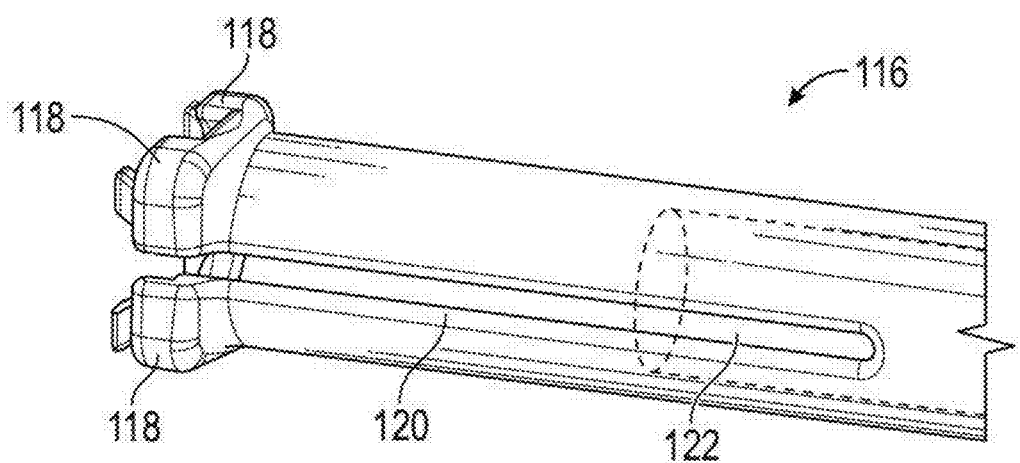

FIG. 27B illustrates one embodiment of an inserter end 116 adapted for securing and inserting the implant 10 into the intervertebral space. The inserter end 116 includes sets of opposed claws 118 that engage pockets on the surface of the implant 10. The claws 118 are able to flex inwardly as they enter the pockets due to slits 120 in the inserter end 116 that provide compliance and flexibility to the claws 118. Once the claws 118 are fully engaged in the pockets, a center portion 122 of the inserter is advanced such that the claws 118 can no longer collapse inwardly to release the implant 10. The implant 10 is thus retained until the center portion 122 is withdrawn.

Figure 28A:
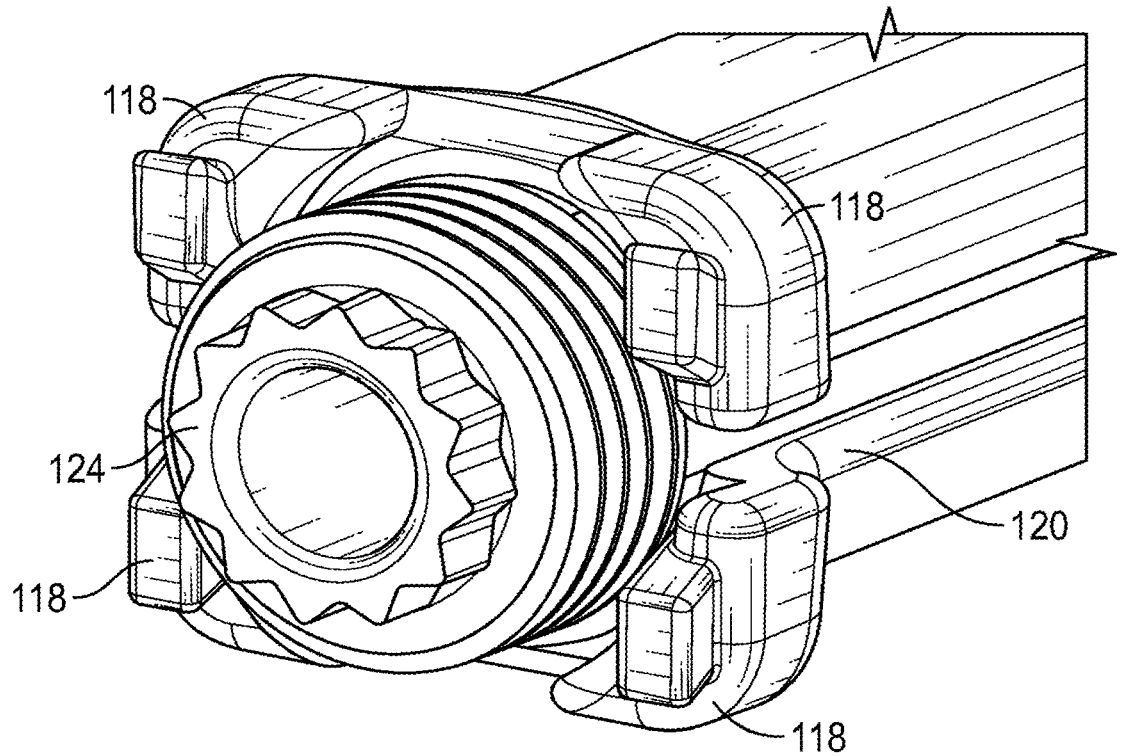
FIGS. 28A and 28B illustrate aspects of an implant inserter.

Because multiple items (the feed tube of the bladder 56, the locking driver, and the claw expander) have to fit through the inserter end 116, radial space is at a premium. Accordingly, in some embodiments, driving interfaces that can transmit relatively large torques while occupying relatively little radial space are used. FIG. 28A shows one embodiment that uses a triple-square drive 124. Hex, Torx, TorxPlus, or some variation thereof are used in alternate embodiments, as is a driver having castellations on the face thereof.

Figure 28B:
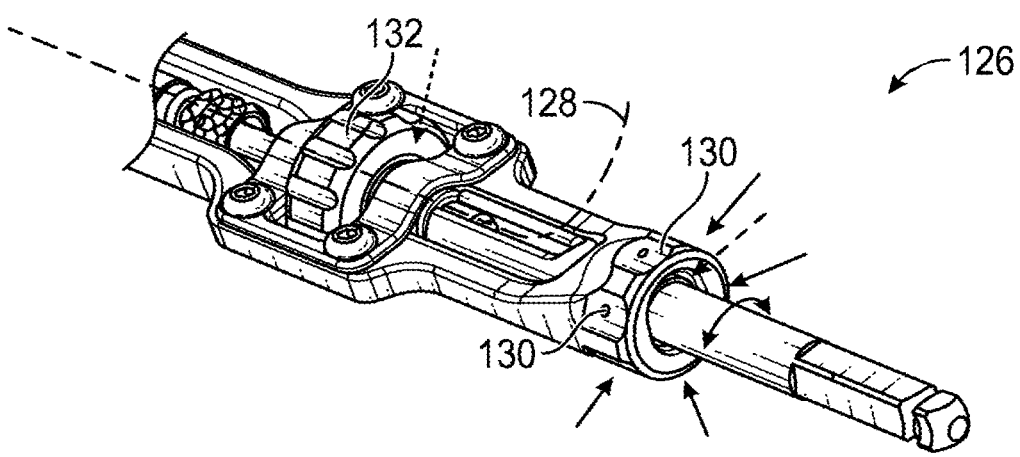

FIG. 28B shows a perspective view of one embodiment of an inserter 126 (with the inserter end 116 omitted). To permit proper placement of the implant 10, it is important to be able to hammer on the back of the inserter 126 without crushing the feed tube of the bladder 56 and to rotate the driver to activate the implant shape-locking mechanism without twisting up the feed tube of the bladder 56 or depressurizing the bladder 56. The inserter 126 of FIG. 28B achieves these objectives by having the top face of the inserter 126 open such that a feed tube 128 can exit from the drive and out to the side without passing through a hammering surface 130.

A thumb wheel 132 engages the driver and allows for initial tightening of the locking mechanism by continuous rotation. For final tightening, a counter-torque is attached to flats 134 of a tail of the instrument and a slotted driver is introduced, still allowing the feed tube 128 to pass and remain under pressure. The slotted driver is limited to a small range of angular motion to prevent the feed tube 128 from being sheared off. Accordingly, final tightening is an incremental process.

Figure 29A:
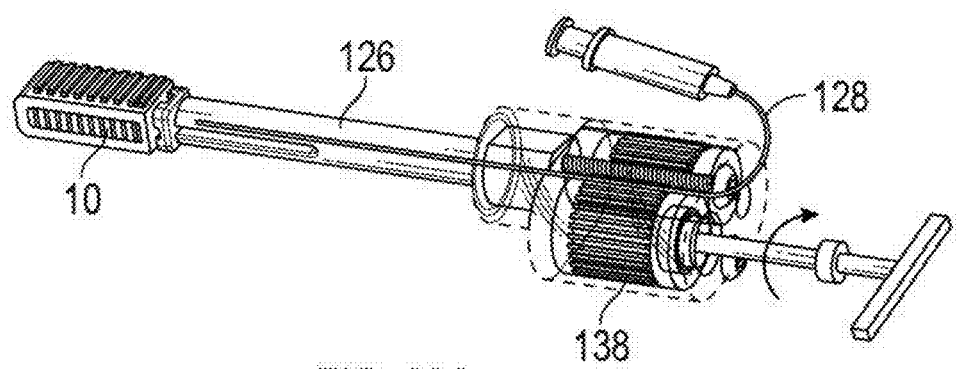
FIGS. 29A and 29B illustrate aspects of implant inserters.
Figure 29B:
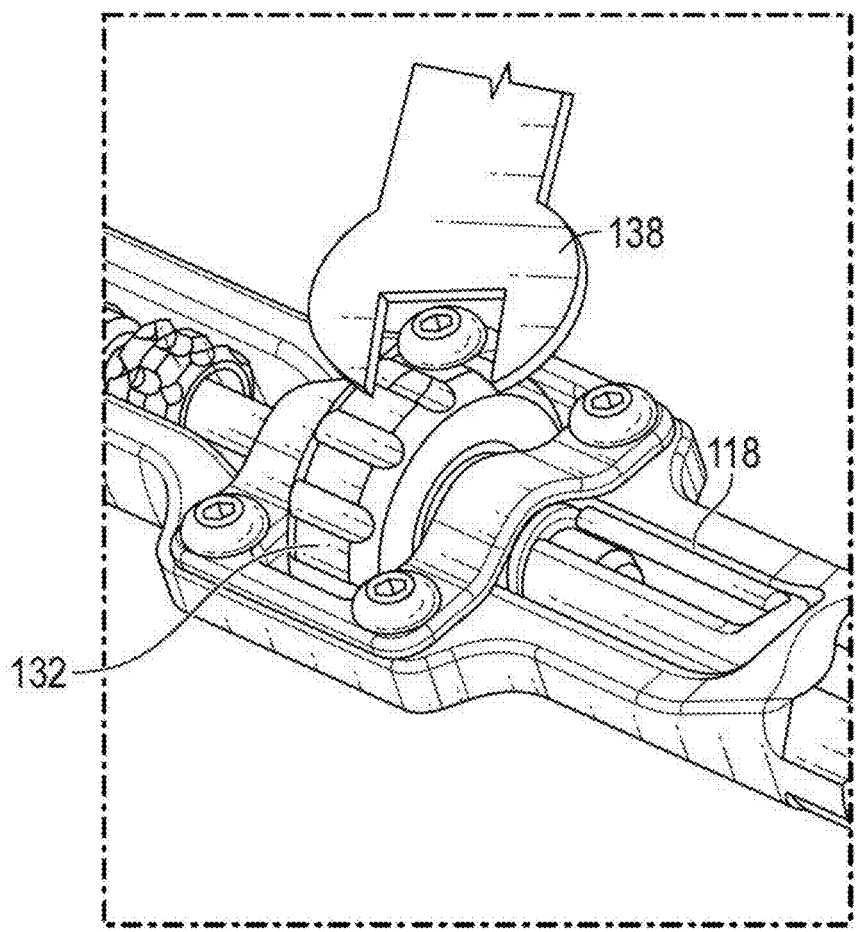
Figure 30A:
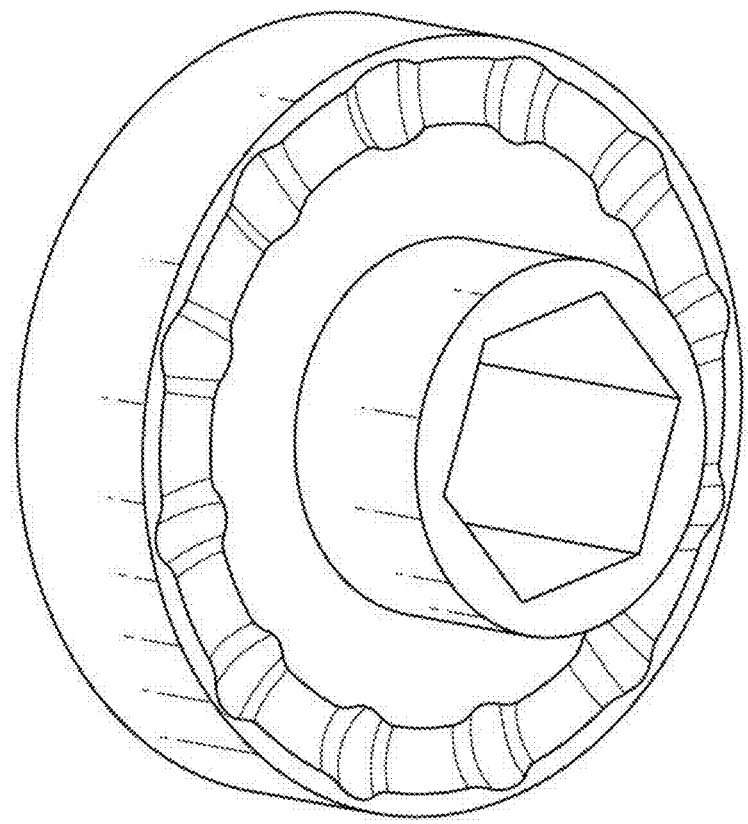
FIGS. 30A and 30B illustrate aspects of implant inserters.

FIG. 29A shows an alternate version of the inserter 126. In this embodiment, a gearbox 136 is used to move the rotation connection off to the side of the feed tube 128. A cap for hammering is provided to the back of the inserter 126. Another solution, as shown in FIG. 29B would utilize an inserter 126 similar to that of FIG. 28B, but fits the thumb wheel 132 with a torque-limiting clutch and then uses a wrench 138 of some sort to rotate the thumb wheel to achieve final torque. In the embodiment of FIG. 29B, it is important that the clutch not overtighten the locking mechanism, but always be able to unlock it. The clutch face shown in FIG. 30A has different entry and exit angles to the depressions in the race, thus allowing for different release torques in the forwards and backwards directions.

Figure 30B:
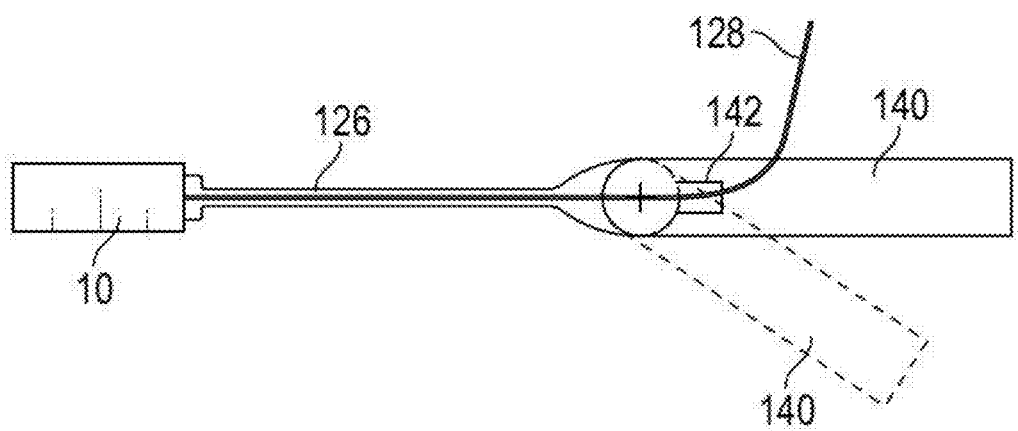

FIG. 30B illustrates an alternate version of the inserter 126. In this embodiment, the inserter 126 has a dual-state handle 140 to protect the feed tube 128 from hammering when the handle 140 is in a straight position, but providing improved access to a driver 142 when the handle 140 is rotated out of the way.

Figure 31:
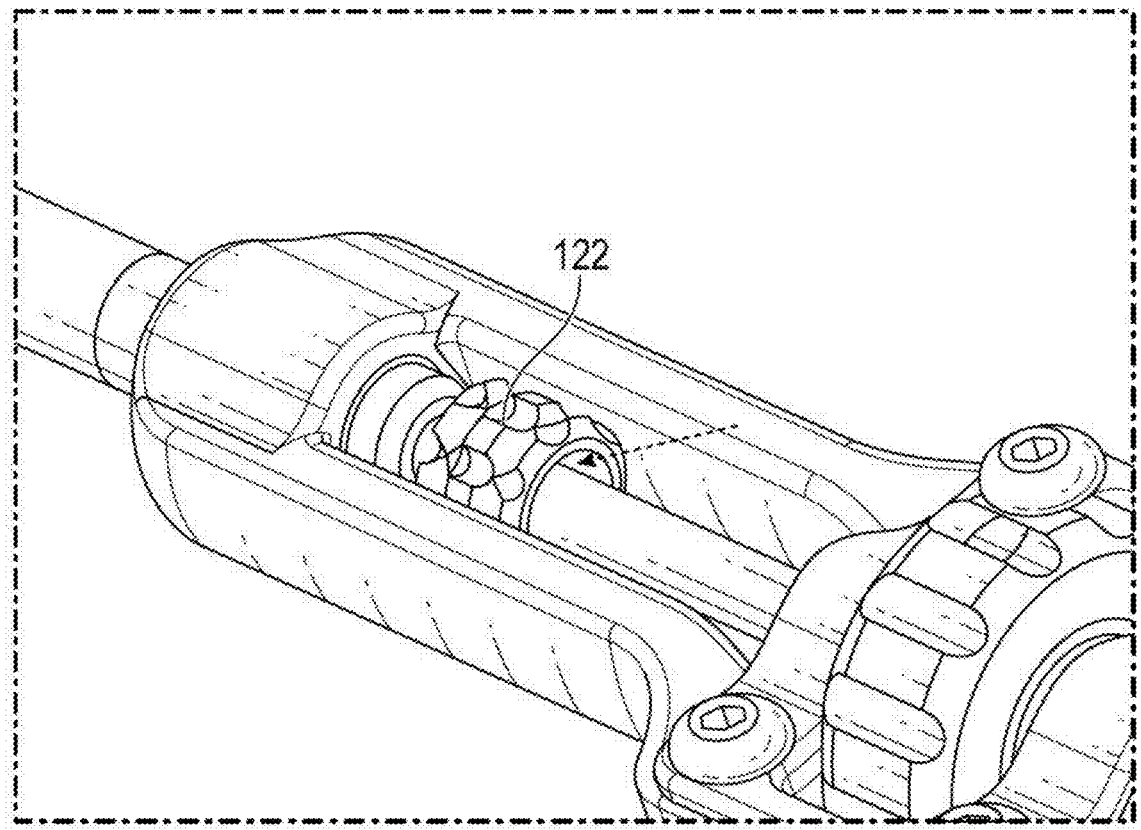
FIG. 31 illustrates aspects of an implant inserter.

As illustrated in FIG. 31, the inserter 126 of some embodiments is designed such that it does not need to be detached from the implant 10 before post packing the implant 10 with bone graft or the like. Instead, after the shape of the implant 10 has been locked, the driver and the bladder 56 can be removed through the internal portion 122 that expands the claws 118 to engage the implant 10. Some sort of fusion-promoting substance can then be packed into the implant through the lumen of the internal portion 122.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. A method for using an expanding, conforming interbody implant, comprising:
   affixing an expanding, conforming interbody implant to an inserter, the implant comprising:
      a frame;
      a first plurality of endplate-contacting segments adapted to each independently extend a variable amount in a superior direction from the frame;
      a second plurality of endplate-contacting segments adapted to each independently extend a variable amount in an inferior direction from the frame; and
      a locking mechanism adapted to lock the first plurality of endplate-contacting segments and the second plurality of endplate-contacting segments in a variety of independently extended positions, whereby each endplate-contacting segment of the first and second plurality of endplate-contacting segments contacts and supports bone adjacent the expandable, conformable interbody implant;
   placing the implant in a desired location using the inserter while the first and second pluralities of endplate-contacting segments are in a retracted position;
   supplying a force that causes each of the first and second pluralities of endplate-contacting segments to extend and generally conform to surfaces above and below the implant; and
   engaging the locking mechanism to secure the first and second pluralities of endplate-contacting segments in a variety of extended and conforming positions.

2. The method as recited in claim 1, wherein the first plurality of endplate-contacting segments is adapted to contact and collectively conform to an inferior endplate of a first vertebral body and wherein the second plurality of endplate-contacting segments is adapted to contact and collectively conform to a superior endplate of a second vertebral body.

3. The method as recited in claim 2, wherein a load between the inferior endplate and the superior endplate is substantially equally distributed among the first and second pluralities of endplate-contacting segments.

4. The method as recited in claim 1, wherein the locking mechanism exerts a lateral compression force among the first and second pluralities of endplate-contacting segments.

5. The method as recited in claim 1, wherein the locking mechanism exerts a lateral compression force between the first plurality of endplate-contacting segments, the second plurality of endplate-contacting segments, and a plurality of cross webs.

6. The method as recited in claim 1, wherein the first and second pluralities of endplate-contacting segments have a limited amount of lateral motion within the frame before the locking mechanism is engaged to lock the first and second pluralities of endplate-contacting segments in their extended positions.

7. The method as recited in claim 1, wherein when the first and second pluralities of endplate-contacting segments are in a retracted position, the implant has a smaller vertical profile for insertion.

8. The method as recited in claim 1, wherein the first and second pluralities of endplate-contacting segments are each interlocked with adjacent segments while permitting relative superior-inferior motion therebetween.

9. The method as recited in claim 1, wherein the first and second pluralities of endplate-contacting segments each comprise a plurality of segments extending along a length of the implant.

10. The method as recited in claim 9, wherein the first and second pluralities of endplate-contacting segments each comprise a plurality of segments extending across a width of the implant.

11. The method as recited in claim 1, wherein the first and second pluralities of endplate-contacting segments comprise a stiffness approximating the stiffness of vertebral bone.

12. The method as recited in claim 11, wherein the first and second pluralities of endplate-contacting segments comprise a coil pack construction.

13. The method as recited in claim 1, wherein the implant is formed of biocompatible substances.

14. The method as recited in claim 1, further comprising an expansion mechanism adapted to apply a superior-directed force to each of the first plurality of endplate-contacting segments and an inferior-directed force to each of the second plurality of endplate-contacting segments before the locking mechanism is engaged.

15. The method as recited in claim 14, wherein the expansion mechanism is adapted to continue providing the superior-directed force and the inferior-directed force while the locking mechanism is engaged.

16. The method as recited in claim 14, wherein the expansion mechanism comprises a bladder disposed in an internal cavity of the implant.

17. The method as recited in claim 14, wherein the expansion mechanism comprises a mechanism selected from the group consisting of:
a bladder;
a plurality of corrugated layers adapted to be moved between nested and offset positions;
a plurality of springs;
a wire disposed on a plurality of pulleys;
a plurality of threaded cylinders; and
a plurality of dimpled layers adapted to be moved between nested and offset positions.

18. The method as recited in claim 1, wherein the frame comprises openings on opposite ends thereof to permit access to an internal space of the implant.

19. The method as recited in claim 1, wherein the implant is adapted to permit application of increased forces in any of an anterior area, a posterior area, a right lateral area, or a left lateral area.

* * * * *

UNITED STATES PATENT AND TRADEMARK OFFICE
CERTIFICATE OF CORRECTION

Page 1 of 1

PATENT NO. : 12,059,352 B2
APPLICATION NO. : 18/089441
DATED : August 13, 2024
INVENTOR(S) : Daniel Manwill and Peter Halverson It is certified that error appears in the above-identified patent and that said Letters Patent is hereby corrected as shown below:

On the Title Page

Item (72) (Inventors), a third inventor, DAVID T. HAWKES, Salt Lake City, UT (US) should be added.

Signed and Sealed this
Twentieth Day of May, 2025

Coke Morgan Stewart
*Acting Director of the United States Patent and Trademark Office*